(12) United States Patent
Pokholok et al.

(10) Patent No.: US 7,556,921 B2
(45) Date of Patent: Jul. 7, 2009

(54) METHODS FOR MAPPING SIGNAL TRANSDUCTION PATHWAYS TO GENE EXPRESSION PROGRAMS

(75) Inventors: Dmitry K. Pokholok, San Diego, CA (US); Richard A. Young, Weston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 11/607,478

(22) Filed: Dec. 1, 2006

(65) Prior Publication Data

US 2007/0196837 A1    Aug. 23, 2007

Related U.S. Application Data

(60) Provisional application No. 60/741,558, filed on Dec. 2, 2005.

(51) Int. Cl.
*C12Q 1/68*   (2006.01)
(52) U.S. Cl. .......................................... 435/6
(58) Field of Classification Search ............ 435/6
See application file for complete search history.

(56) References Cited

U.S. PATENT DOCUMENTS

| | | | |
|---|---|---|---|
| 5,424,188 A | 6/1995 | Schneider et al. | |
| 6,109,776 A | 8/2000 | Haas | |
| 6,410,233 B2 | 6/2002 | Mercola et al. | |
| 6,410,243 B1 | 6/2002 | Wyrick et al. | |
| 6,982,145 B1 | 1/2006 | Mercola et al. | |

FOREIGN PATENT DOCUMENTS

| | | | |
|---|---|---|---|
| WO | WO0116378 A2 | 3/2001 | |
| WO | WO0214550 A2 | 2/2002 | |
| WO | WO2004053106 A2 | 6/2004 | |
| WO | WO2004087965 A2 | 10/2004 | |
| WO | WO2004097577 A2 | 11/2004 | |
| WO | WO2005054461 A2 | 6/2005 | |

OTHER PUBLICATIONS

Zeitlinger et al., Cell, 113, 395-404, 2003.*
Aparicio et al., "Components and dynamics of DNA replication complexes in *S. cerevisiae*: redistribution of MCM proteins and Cdc45p during S phase," 1997, Cell, 91(3):59-69.
Barany, "The ligase chain reaction in a PCR world," 1991, PCR Methods Appl., 1(1):5-16.
Bar-Joseph et al., "Computational discovery of gene modules and regulatory networks", Nat. Biotechnol., 2003, 21(11):1337-1342.
Bigler et al., "Isolation of a thyroid hormone-responsive gene by immunoprecipitation of thyroid hormone receptor-DNA complexes," 1994, Mol. Cell Biol., 14(11):7621-7632.
Bigler et al., "Novel location and function of a thyroid hormone response element," 1995, EMBO J., 14(22):5710-5723.
Blat et al., "Cohesins bind to preferential sites along yeast chromosome III, with differential regulation along arms versus the centric region," 1999, Cell, 98(2):249-259.
Botquin et al., "New POU dimer configuration mediates antagonistic control of an osteopontin preimplantation enhancer by Oct. 4 and Sox-2," 1998, Genes Dev., 12(13):2073-2090.
Cohen-Kaminsky et al., "Chromatin immunoselection defines a TAL-1 target gene," 1998, EMBO J., 17(17):5151-5160.
De Risi et al., "Exploring the metabolic and genetic control of gene expression on a genomic scale," 1997, Science, 278(5338):680-686.
Deveaux et al., "p45 NF-E2 regulates expression of thromboxane synthase in megakaryocytes," 1997, EMBO J, 16(18):5654-5661.
Gould et al., "Connectin, a target of homeotic gene control in Drosophila ," 1992, Development, 116(4):1163-1174.
Gould et al., "Targets of homeotic gene control in Drosophila," 1990, Nature, 348(6299):308-312.
Graba et al., "Drosophila Hox complex downstream targets and the function of homeotic genes," 1997, BioEssays, 19(5):379-388.
Graba et al., "DWnt-4, a novel Drosophila Wnt gene acts downstream of homeotic complex genes in the visceral mesoderm," 1995, Development, 121(1):209-218.
Graba et al., "Homeotic control in Drosophila; the scabrous gene is an in vivo target of Ultrabithorax proteins," 1992, EMBO J., 11(9):3375-3384.
Grandori et al., "Myc-Max heterodimers activate a DEAD box gene and interact with multiple E box-related sites in vivo," EMBO J., 15(16):4344-4357.
Hallahan et al., "C-jun and Egr-1 participate in DNA synthesis and cell survival in response to ionizing radiation exposure," 1995, J. Biol. Chem. 270(51):30303-30309.
Hartemink et al., "Combining location and expression data for principled discovery of genetic regulatory network models," 2002, Pac Symp. Biocomput., 437-449.
Hecht et al., "Spreading of transcriptional repressor SIR3 from telomeric heterochromatin," 1996, Nature, 383(6595):92-96.
Holstege et al., "Dissecting the regulatory circuitry of a eukaryotic genome," 1998, Cell, 95(5):717-728.
Kohwi-Shigematsu et al., "Identification of base-unpairing region-binding proteins and characterization of their in vivo binding sequences," 1998, Methods Cell Biol., 53:323-354.
Kumar et al., "Forkhead transcription factors, Fkh1p and Fkh2p, collaborate with Mcm1p to control transcription required for M-phase," 2000, Curr. Biol. 10(15)896-906.

(Continued)

*Primary Examiner*—Maryam Monshipouri
(74) *Attorney, Agent, or Firm*—James S. Keddie; Bozicevic, Field & Francis LLP

(57) ABSTRACT

The invention relates to improved methods of identifying the gene expression programs that are regulated by a signal transduction pathway. The invention also provides methods of identifying agents which modulate signal transduction pathway. The invention also provides improved methods of isolating DNA fragments to which a protein of interest is bound, and genome-wide location analysis methods employing these improved isolation methods.

22 Claims, 7 Drawing Sheets
(5 of 7 Drawing Sheet(s) Filed in Color)

OTHER PUBLICATIONS

Lee et al., "Transcriptional regulatory networks in *Saccharomyces cerevisiae*," 2002, Science, 298(5594):799-804.

Mukherjee et al., "Rapid analysis of the DNA-binding specificities of transcription factors with DNA microarrays," 2004, Nat. Genet., 36(12):1331-1339.

Nickerson et al., "The nuclear matrix revealed by eluting chromatin from a cross-linked nucleus," 1997, Proc. Natl. Acad. Sci. USA, 94(9):4446-4450.

Odom et al., "Control of pancreas and liver gene expression by HNF transcription factors," 2004, Science, 303 (5662):1378-1381.

Orlando et al., "Analysis of chromatin structure by in vivo formaldehyde cross-linking," 1997, Methods, 11(2):205-214.

Orlando et al., "Mapping Polycomb-repressed domains in the bithorax complex using in vivo formaldehyde cross-linked chromatin," 1993, Cell, 75(6):1187-1198.

Orlando, "Mapping chromosomal proteins in vivo by formaldehyde-crosslinked-chromatin immunoprecipitation," 2000, Trends Biochem. Sci., 25(3):99-104.

Pradel et al., "From selectors to realizator," 1998, Int. J. Dev. Biol. 42(3):417-421.

Reid et al., "Coordinate regulation of yeast ribosomal protein genes is associated with targeted recruitment of Esa1 histone acetylase," 2000, Mol. Cell, 6(6):1297-1307.

Ren et al., "Genome-wide location and function of DNA binding proteins," 2000, Science, 290(5500):2306-2309.

Schena et al., "Microarrays: biotechnology's discovery platform for functional genomics," 1998, Trends Biotechnol., 16(7):301-306.

Schouten, "Hybridization selection of covalent nucleic acid-protein complexes. 2. Cross-linking of proteins to specific *Escherichia coli* mRNAs and DNA sequences by formaldehyde treatment of intact cells," 1985, J. Biol. Chem., 260(17):9929-9935.

Solomon et al., "Formaldehyde-mediated DNA-protein crosslinking: a probe for in vivo chromatin structures," 1985, Proc. Natl. Acad. Sci. USA, 82(19):6470-6474.

Solomon et al., "Mapping protein-DNA interactions in vivo with formaldehyde: evidence that histone H4 is retained on a highly transcribed gene," 1988, Cell, 53(6):937-947.

Takahashi et al., "Application of the chromatin immunoprecipitation method to identify in vivo protein-DNA associations in fission yeast," 2000, Sci. STKE, 2000(56): PL1.

Tanaka et al., "Loading of an Mcm protein onto DNA replication origins is regulated by Cdc6p and CDKs," 1997, Cell, 90(4):649-660.

Tomotsune et al., "A mouse homologue of the Drosophila tumour-suppressor gene l(2)gl controlled by Hox-C8 in vivo," 1993, Nature, 365(6441):69-72.

Walter et al., "Measurement of in vivo DNA binding by sequence-specific transcription factors using UV cross-linking," 1997, Methods, 11(2):215-224.

Weinmann et al., "Isolating human transcription factor targets by coupling chromatin immunoprecipitation and CpG island microarray analysis," 2002, Genes Dev., 16(2):235-244.

Wyrick et al., "Deciphering gene expression regulatory networks," 2002, Curr. Opin. Genet. Dev., 12(2):130-136.

Zhu et al., "Two yeast forkhead genes regulate the cell cycle and pseudohyphal growth," 2000, Nature, 406(6791):90-94.

\* cited by examiner

US 7,556,921 B2

METHODS FOR MAPPING SIGNAL TRANSDUCTION PATHWAYS TO GENE EXPRESSION PROGRAMS

CROSS-REFERENCE TO RELATED APPLICATIONS

Pursuant to 35 U.S.C. § 119 (e), this application claims priority to the filing date of U.S. Provisional Patent Application Ser. No. 60/741,558 filed on Dec. 2, 2005; the disclosure of which application is herein incorporated by reference.

GOVERNMENT RIGHTS

This invention was made with government support under federal grant no. A1055021 awarded by the National Institutes of Health. The United States Government may have certain rights in this invention.

INTRODUCTION

Signal transduction is any process by which a cell recognizes a signal or stimulus and transmits the information such that a response can be made to the stimulus. The environment of a cell contains many molecules that can act as signals or stimuli that influence the behavior of the cell. For example, the response to a change in glucose concentration outside cells can be recognized through a receptor-ligand interaction and transmitted through the protein kinase A (PKA) pathway, leading to a change in phosphorylation state of transcription factors and other proteins, which in turn can lead to a change in gene expression and metabolism within the cell.

Processes referred to as signal transduction often involve a sequence of biochemical reactions performed by various proteins inside the cell. This sequence of biochemical reactions forms a pathway, and the mapping of such pathways is important because they lead to a molecular understanding of cellular responses to stimuli. Improved understanding of signal transduction pathways is also important because these pathways can be modified by small molecule and protein therapeutics, thus providing an approach to therapy of various diseases such as cancer.

Stimulation of signal transduction pathways causes modifications in gene expression programs, but exactly how this modification is accomplished is unknown. The pathway maps generally identify the enzymes responsible for the sequence of biochemical that allow the reactions that make up the signal transduction pathway, but these pathways have not been mapped precisely to the set of genes that are directly affected by the pathway. Thus, we have incomplete maps of signaling pathways in biology.

A need remains, therefore, for developing methods to identify the genes whose expression is regulated by a signaling pathway. The present invention provides these and other methods.

SUMMARY

One aspect of the invention provides methods of identifying genes whose expression is regulated by a signaling pathway. The invention is based, in part, on the surprising discovery by Applicants that key members of signaling pathways that do not encode transcription factors are physically associated with genes that they regulate via the pathway. Applicants have discovered that key signaling members associate with the promoter and/or the transcribed regions of the genes that are regulated by the signaling pathway.

Another aspect of the invention provides improved methods of isolating DNA fragments to which a protein is bound in a cell. In one embodiment, the protein and DNA are cross-linked in a solution comprising paraformaldehyde, and optionally also comprising a second cross-linking agent, such as formaldehyde. The improved methods of isolating DNA fragments may be combined with immunoprecipitations of the protein/DNA-fragments and genome-wide location analysis.

BRIEF DESCRIPTION OF THE FIGURES

The patent or application file contains at least one drawing executed in color. Copies of this patent application publication with color drawing(s) will be provided by the U.S. Patent and Trademark Office upon request and payment of the necessary fee.

(FIG. 1A) The Hog MAPK pathway in S. cerevisiae. (FIG. 1B) Genes that are bound by Hog1p (table S2) and induced during osmotic stress (with NaCl or KCl). The maximum ChIP enrichment of Hog1p along each gene before and 5 min after NaCl addition are shown in blue. Previously identified target genes are indicated by asterisks. Changes in expression in response to osmotic stress (red for induction and green for repression) of Hog1p-bound genes are displayed for wild-type cells (WT) and for a strain lacking Hog1p (hog1). (FIG. 1C) Occupancy of the STL1 gene by Hog1p in control medium [yeast extract, peptone, and dextrose (YPD)] (blue line) and 5 min after the induction of osmotic stress with 0.4 M NaCl (red line), based on merged duplicate data from genome-wide ChIP-Chip analyses. The genomic positions of probe regions and their enrichment ratios are displayed on the x and y axes, respectively. Open reading frames (ORFs) are depicted as gray rectangles, and arrows indicate the direction of transcription.

(FIG. 2A) The pheromone response MAPK pathway in S. cerevisiae. (FIGS. 2B, 2D, and 2F) Genes bound by Fus3p (FIG. 2B), Kss1p (2D), and Ste5p (2F) at high confidence (tables S3 to S5) that are induced after alpha pheromone treatment. The occupancy of Fus3p, Kss1p, and Ste5p is shown as maximum ChIP enrichment along each gene in blue. Changes in the expression of these genes during pheromone treatment relative to untreated control samples are displayed in red (induction) and green (repression). (FIGS. 2C, 2E, and 2G) Occupancy of the AGA1 gene by Fus3p (2C), Kss1p (2E), and Ste5p (2G) in control YPD medium (blue line) and 5 min after exposure to alpha pheromone (5 µg/ml) (red line), based on merged duplicate or triplicate data from genome-wide ChIP-Chip analyses.

(FIG. 3A) The cAMP/PKA signaling pathway in S. cerevisiae. (FIG. 3B) Occupancy of Tpk1p at a portion of chromosome VII, containing the PMA1 and LEU1 genes, in the presence of glucose based on data from genome-wide ChIP-Chip analyses. The transcriptional frequency of the corresponding ORF is indicated as mRNA per hour underneath each ORF. (FIG. 3C) Average Tpk1p enrichment for classes of different transcriptional frequencies [determined by means of metagene analysis (D. K. Pokholok et al., Cell 122, 517 (2005))]. The genome's 5324 genes were divided into five classes according to their transcriptional rate (F. C. Holstege et al., Cell 95, 717 (1998)). A fixed length was assigned to each ORF and intergenic region, and probes were assigned to the nearest relative position and averaged for each class. (FIG. 3D) Tpk1p occupancy at a portion of chromosome XII, containing the YEF3 gene whose transcription is substantially reduced during growth in medium containing glycerol (blue line) as compared to that in control medium (YPD) containing glucose (red line). (FIG. 3E) Tpk1p occupancy at GAL1-10 locus in glucose-containing medium (blue line) after the addition of galactose (red line with solid circles) and of galactose in the absence of Gal4p (gal4) (red line with open circles). (FIG. 3F) Tpk2p occupancy at the promoter of the RPS11B gene during oxidative stress and in control medium (YPD) containing glucose. FIG. 3G shows the catalytic Tpk1 and the regulatory Bcy1 subunits of PKA occupy transcribed regions of active genes.

DEFINITIONS

Figure 1A:
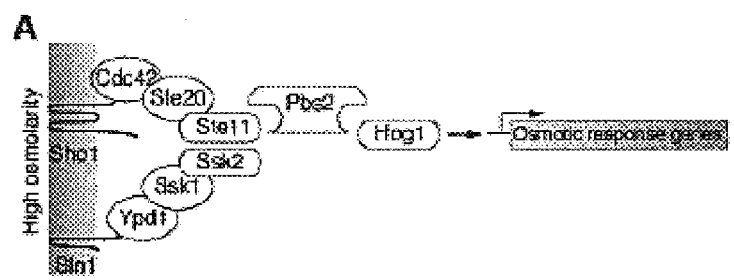
FIGS. 1A to 1C. Recruitment of Hog1p to promoters and transcribed regions of genes activated by osmotic stress.

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

A "patient" or "subject" to be treated by the method of the invention can mean either a human or non-human animal, preferably a mammal.

The term "encoding" comprises an RNA product resulting from transcription of a DNA molecule, a protein resulting from the translation of an RNA molecule, or a protein resulting from the transcription of a DNA molecule and the subsequent translation of the RNA product.

The term "expression" is used herein to mean the process by which a polypeptide is produced from DNA or RNA. The process involves the transcription of the gene into mRNA and the translation of this mRNA into a polypeptide. Depending on the context in which used, "expression" may refer to the production of RNA, protein or both.

"Recombinant" when used with reference, e.g., to a nucleic acid, cell, virus, plasmid, vector, or the like, indicates that these elements have been modified by the introduction of an exogenous, non-native nucleic acid or the alteration of a native nucleic acid, or have been derived from a recombinant nucleic acid, cell, virus, plasmid, or vector. Recombinant protein refers to a protein derived from a recombinant nucleic acid, virus, plasmid, vector, or the like.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer). Transcriptional regulators may contain DNA-binding domains.

The term "microarray" refers to an array of distinct polynucleotides or oligonucleotides present on a substrate, such as paper, nylon or other type of membrane, filter, chip, glass slide, or any other suitable solid support, typically in the form of "spots" located at microscopic distances from adjacent spots.

A probe that is "labeled" is detectable, either directly or indirectly, by spectroscopic, photochemical, biochemical, immunochemical, isotopic, or chemical means. For example, useful labels include $^{32}P$, $^{33}P$, $^{35}S$, $^{14}C$, $^{3}H$, $^{125}I$, stable isotopes, fluorescent or chemiluminescent dyes and fluorettes (Rozinov and Nolan (1998) Chem. Biol 5:713-728; Molecular Probes, Iac. (2003) Catalogue, Molecular Probes, Eugene Oreg.), electron-dense reagents, enzymes and/or substrates, e.g., as used in enzyme-linked immunoassays as with those using alkaline phosphatase or horse radish peroxidase, tags that are recognizable by binding agents such as antibodies or complementary nucleic acids, etc. The label or detectable moiety is typically bound, either covalently, through a linker or chemical bond, or through ionic, van der Waals or hydrogen bonds to the molecule to be detected. It will be appreciated that "labeled" can also encompass attachment or incorporation of quenchers and quenchable moieties, and that detection can be accomplished by detecting quenching rather than emission of a signal. "Radiolabeled" refers to a compound to which a radioisotope has been attached through covalent or non-covalent means or that incorporates a radioisotope. A "fluorophore" is a compound or moiety that absorbs radiant energy of one wavelength and emits radiant energy of a second, longer wavelength.

A "labeled nucleic acid probe or oligonucleotide" is one that is bound, either covalently, through a linker or a chemical bond, or non-covalently, through ionic, van der Waals, electrostatic, or hydrogen bonds to a label such that the presence of the probe can be detected by detecting the presence of the label bound to the probe. The probes are, in certain embodiments, directly labeled as with isotopes, chromophores, fluorophores, chromogens, or indirectly labeled such as with biotin to which a streptavidin complex or avidin complex can later bind. It will be appreciated that the probe that binds to a target nucleic acid need not itself be labeled with one of the afore-mentioned moieties but may instead contain a portion that serves as a binding site for a second nucleic acid probe. For example, the invention encompasses use of branched nucleic acid technology (e.g., bDNA technology) and other signal amplification methods.

A "nucleic acid probe" is a nucleic acid capable of binding to a target nucleic acid of complementary sequence, usually through complementary base pairing, e.g., through hydrogen bond formation. A probe may include natural, e.g., A, G, C, or T, or modified bases, e.g., 7-deazaguanosine, inosine, etc. The bases in a probe can be joined by a linkage other than a phosphodiester bond. Probes can be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions.

"Polymerase chain reaction" (PCR) refers, e.g., to a procedure or product where a specific region or segment of a nucleic acid is amplified, and where the segment is bracketed by primers used by DNA polymerase (Bernard and Wittwer (2002). Clin. Chem. 48:1178-1185; Joyce (2002) Methods Mol. Biol. 193:83-92; Ong and tvine (2002) Hematol. 7:59-67).

A "promoter" is a nucleic acid sequence that directs transcription of a nucleic acid. A promoter includes nucleic acid sequences near the start site of transcription, e.g., a TATA box, see, e.g., Butler and Kadonaga (2002) Genes Dev. 16:2583-2592; Georgel (2002) Biochem. Cell Biol. 80:295-300. A promoter also optionally is associated with distal enhancer or repressor elements, which can be located as much as several thousand base pairs on either side from the start site of transcription. A "constitutive" promoter is a promoter that is active under most environmental and developmental conditions, while an "inducible", promoter is a promoter that is active or activated under, e.g., specific environmental or developmental conditions.

"Small molecule" is defined as a molecule with a molecular weight that is less than 10 kD, typically less than 2 kD, and preferably less than 1 kDa. Small molecules include, but are not limited to, inorganic molecules, organic molecules, organic molecules containing an inorganic component, molecules comprising a radioactive atom, synthetic molecules, peptide mimetics; and antibody mimetics. As a therapeutic, a small molecule may be more permeable to cells, less susceptible to degradation, and less apt to elicit an immune response than large molecules. Small molecule toxins are described, see, e.g., U.S. Pat. No. 6,326,482 issued to Stewart, et al.

The term "genome" refers to all nucleic acid sequences (coding and non-coding) and elements present in any virus, single cell (prokaryote and eukaryote) or each cell type in a metazoan organism, e.g. those sequences that are heritable or were inherited from an ancestor of the virus or cell. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism. For example, the human genome consists of approximately $3.0 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence. In certain aspects, a "genome" refers to nuclear nucleic acids, excluding mitochondrial nucleic acids; however, in other aspects, the term does not exclude mitochondrial nucleic acids. In still other aspects, the "mitochondrial genome" is used to refer specifically to nucleic acids found in mitochondrial fractions.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other nucleic acids that are C-glycosides of a purine or pyrimidine base, polypeptides (proteins) or polysaccharides (starches, or polysugars), as well as other chemical entities that contain repeating units of like chemical structure.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "oligonucleotide" as used herein denotes single stranded nucleotide multimers of from about 10 to 100 nucleotides and up to 200 nucleotides in length.

The term "functionalization" as used herein relates to modification of a solid substrate to provide a plurality of functional groups on the substrate surface. By a "functionalized surface" is meant a substrate surface that has been modified so that a plurality of functional groups are present thereon.

The terms "reactive site", "reactive functional group" or "reactive group" refer to moieties on a monomer, polymer or substrate surface that may be used as the starting point in a synthetic organic process. This is contrasted to "inert" hydrophilic groups that could also be present on a substrate surface, e.g., hydrophilic sites associated with polyethylene glycol, a polyamide or the like.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide or other substrate scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1×SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, such as less than about 3-fold more. Other stringent hybridization conditions are known in the art and may also be employed, as appropriate.

Sensitivity is a term used to refer to the ability of a given assay to detect a given analyte in a sample, e.g., a nucleic acid species of interest. For example, an assay has high sensitivity if it can detect a small concentration of analyte molecules in sample. Conversely, a given assay has low sensitivity if it only detects a large concentration of analyte molecules (i.e., specific solution phase nucleic acids of interest) in sample. A given assay's sensitivity is dependent on a number of parameters, including specificity of the reagents employed (e.g., types of labels, types of binding molecules, etc.), assay conditions employed, detection protocols employed, and the like. In the context of array hybridization assays, such as those of the present invention, sensitivity of a given assay may be dependent upon one or more of: the nature of the surface immobilized nucleic acids, the nature of the hybridization and wash conditions, the nature of the labeling system, the nature of the detection system, etc.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, nucleic acid or protein translocation, direct activation (or inhibition) of a transcriptional factor and/or activation of nucleic acid or protein degradation pathways. A "signal transduction pathway" refers to the components involved in "signal transduction" of a particular signal into a cell. The term "endogenous signal transduction pathway" indicates that some or all of the components of the signal transduction pathway are naturally-occurring components of the cell. An example of such a pathway is the endogenous pheromone response pathway of yeast.

The phrase "operably linked" when referring to region of the genome can be part of a gene of interest or outside of, e.g., proximal to the gene of interest. As such, in certain embodiments, the gene, or its transcriptional start site, may be in physical proximity to the region of the genome which is considered operably linked thereto, or the region that is operably linked to the gene may actually be located 3' of the transcriptional start site. As such, a region of interest may be operably linked to a gene and be upstream or downstream from the transcriptional start site of the gene.

As used herein, the term "extracellular signal" is intended to encompass molecules and changes in the environment that are transduced intracellularly, e.g., via cell surface proteins that interact, directly or indirectly, with the extracellular signal. An extracellular signal or effector molecule includes any compound or substance that in some manner alters the activity of a cell surface protein. In certain embodiments the term includes molecules such as glucorticoids that enter cells and modulate the activity of cytoplasmic and/or nuclear proteins, molecules that are internalized by the cell, etc. Examples of such signals include, but are not limited to, ions, molecules such as acetylcholine and other neurotransmitters, growth factors and hormones, cytokines, nutrients, amino acids, lipids, sugars and nucleotides that bind to cell surface and/or intracellular receptors and ion channels and modulate the activity of such receptors and channels. The term, "extracellular signal" also includes both identified and as yet unidentified substances that modulate the activity of a cellular receptor, and thereby influence intracellular functions. Such extracellular signals include currently used and potential pharmacological agents that may be used to treat specific diseases by modulating the activity of specific cell surface receptors.

DETAILED DESCRIPTION

The invention relates to improved methods of identifying the gene expression programs that are regulated by a signal transduction pathway. The invention also provides methods of identifying agents which modulate signal transduction pathways. The invention also provides improved methods of isolating DNA fragments to which a protein of interest is bound, and genome-wide location analysis methods employing these improved isolation methods.

Before the present invention is described in greater detail, it is to be understood that this invention is not limited to particular embodiments described, as such may vary. It is also to be understood that the terminology used herein is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, suitable methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

In the event that one or more of the incorporated literature and similar materials differs from or contradicts this application, including but not limited to defined terms, term usage, described techniques, or the like, this application controls.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The terms "approximately" or "about" in reference to a number generally includes numbers that fall within a range of 5%, or in certain embodiments within a range of 1% in either direction of the number (i.e., greater than or less than the number) unless otherwise stated or where context dictates otherwise (e.g., where by definition it is not possible to exceed 100% of a value).

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. Furthermore, where the present disclosure describes methods, it should be understood that the invention includes products produced according to those methods, and methods of using the products. For example, the invention provides arrays having one or more signal transduction proteins bound to one or more nucleic acids of the array and generated according to the methods described herein, etc.

I. Overview

Most pathway maps end in the cytoplasm of the cell rather than the nucleus. Those that end in the nucleus do not end at specific genes, but rather at a few transcription factors. Applicants have discovered that key components of activated signaling pathways occupy the set of genes they regulate and can be captured at those genes by using chromatin immunoprecipitation combined with DNA microarrays (also known as genome-wide location analysis or ChIP-on-Chip). With this method, signal transduction pathways can be physically mapped to gene expression programs. Such pathway information will benefit drug development because it can reveal the pathways by which cells are reprogrammed during the response to stimuli in health and disease, including those stimuli produced by therapeutics themselves.

One aspect of the invention provides methods of identifying at least one gene that is regulated by a signaling pathway. One aspect provides a method of identifying at least one gene that is regulated by a signaling pathway, wherein the signaling pathway comprises at least one polypeptide lacking a DNA binding domain, the method comprising the steps of: (a) producing a mixture comprising DNA fragments to which the polypeptide is bound in a cell; (b) isolating one or more DNA fragments to which the polypeptide is bound from the mixture produced in step (a); (c) identifying regions of the genome which are complementary to the DNA fragments isolated in step (b); (d) identifying at least one gene operably-linked to a region of the genome identified in step (b); thereby identifying genes to which the polypeptide of interest binds. In certain embodiments, the polypeptide of interest is a protein that lacks an art-characterized "DNA binding domain" or "motif," i.e., lacks an art accepted DNA binding domain, but nonetheless binds to, either directly or in conjunction with other factors, genomic DNA. As such, the phrase "lacking a DNA binding domain," does not mean that the polypeptide of interest does not bind to genomic DNA, either directly or in combination with one or more additional factors.

In one embodiment, the signaling pathway is a pathway which is activated by the binding of a ligand to a transmembrane receptor. In one embodiment, the polypeptide or protein member of the pathway that is of interest is a component of the signal transduction pathway is an enzyme. In one embodiment, the enzyme hydrolyses ATP or GTP. In one embodiment, the protein is a kinase, such as a MAPK.

In one embodiment, the method comprises, between steps (b) and (c), generating a probe from the one or more of the isolated DNA fragments. In another embodiment, the probe is labeled with a fluorescent moiety or label. In one embodiment, step (c) comprises combining the probe with one or more sets of distinct nucleic acid, e.g., oligonucleotide, features bound to a surface of a solid support (e.g., in the form of an addressable array), wherein the distinct nucleic acid features are each complementary to a region of the genome, under conditions in which specific hybridization between the probe and the nucleic acid features can occur, and detecting said hybridization, wherein hybridization between the labeled probe and a nucleic acid feature relative to a suitable control indicates that the signal transduction protein binds to the region of the genome to which the sequence of the nucleic acid feature is complementary. In another embodiment, one or more sets of the distinct nucleic acid, e.g., oligonucleotide, features are complementary to locations in the genome that are substantially evenly spaced. In another embodiment, the distinct nucleic acid, e.g., oligonucleotide, features are complementary to adjacent regions in the genome spaced from 10 bp to 20 kb of each other. In one embodiment, the nucleic acid, e.g., oligonucleotide, features comprise DNA or RNA or modified forms thereof. In one embodiment, the modified forms of DNA are PNA or LNA molecules. In one embodiment, the nucleic acid, e.g., oligonucleotide, features comprise nucleic acids that range in size from about 20 nt to about 200 nt in length. In one embodiment, the nucleic acids range in size from about 20 to about 100 nt in length. In one embodiment, the nucleic acids range in size from about 40 to about 80 nt in length.

In one embodiment, the nucleic acid, e.g., oligonucleotide, features bound to a surface of a solid support include sequences representative of locations distributed across at least a portion of a genome. In one embodiment, the locations have a uniform spacing across at least a portion of a genome. In another embodiment, the locations have a non-uniform spacing across at least a portion of a genome. In another embodiment, the one or more sets of nucleic acid, e.g., oligonucleotide, features bound to a surface of a solid support samples the portion of the genome about every 20 Kb or more frequently. In another embodiment, the one or more sets of nucleic acid, e.g., oligonucleotide, features bound to a surface of a solid support samples at least a portion of the genome about every 2 Kb or more frequently. In yet another embodiment, the one or more sets of nucleic acid, e.g., oligonucleotide, features bound to a surface of a solid support samples at least a portion of the genome about every 0.5 Kb or more frequently.

In yet one embodiment, the portion of the genome comprises at least 20% of the genome. In one embodiment, the portion of the genome comprises regions of at least at least 20% of chromosomes in the genome. In another embodiment, at least one set of distinct nucleic acid, e.g., oligonucleotide, features comprises distinct oligonucleotide features that correspond to non-coding genomic regions. In another embodiment, at least 50% of the sets of distinct oligonucleotide features are complementary to non-promoter regions.

In one embodiment, at least one set of distinct nucleic acid, e.g., oligonucleotide, features comprises distinct oligonucleotide features that correspond to coding genomic regions. In another embodiment, at least 50% of the distinct nucleic acid, e.g., oligonucleotide, features that correspond to coding genomic regions do not include entire open reading frames. In one embodiment, the solid support is a planar substrate such, as glass. In one embodiment, the sets of distinct nucleic acid, e.g., oligonucleotide, features bound to a solid surface comprise an array, e.g., an addressable array, where the array may be a tiled array.

In one embodiment, steps (a) and (b) are performed in a first location, and steps (c) and/or (d) is performed in a second location, wherein the first location is remote to the second location. In one embodiment, the DNA fragments to which the signal transduction protein is bound from the mixture produced in step (a), or the labeled probes derived from said DNA fragments, are delivered from the first location to the second location. In another embodiment, the method includes a data transmission step between the first location and the second location. In one embodiment, the data transmission step occurs via an electronic communication link, such as the internet.

In one embodiment, the method further includes a data transmission step in which a result from identifying regions of a genome is transmitted from the second location to the first location. In another embodiment, the data transmission step from the second location to the first location includes (i) one or more data transmission substeps from the second location to one or more intermediate locations; and (b) one or more data transmission substeps from one or more intermediate locations to the first location, wherein the intermediate locations are remote to both the first and second locations. In one embodiment, the data transmission step occurs via an electronic communication link. In one embodiment, the data communication link is the Internet.

In one embodiment, the genome is from a eukaryotic cell. In another embodiment, the cell is a metazoan cell. In another embodiment, the cell is a mammalian cell. In one embodiment, the cell is a primary cell. In one embodiment the cell is derived from a blood sample. In one embodiment, the cell is derived from a tissue biopsy. In one embodiment, the issue biopsy is from a subject afflicted with, or suspected of being afflicted with, a disorder. In one embodiment, the cell is a human cell. In another embodiment, the cell is a yeast cell.

In another embodiment, the cell has been treated with an agent. In one embodiment the cell has been isolated from a subject who has been treated with an agent. In one embodiment, the agent binds to one or more signal transduction proteins in the cell (which includes cell surface proteins), changes their expression level, or modulates the biochemical activity of the signaling components. Biochemical activities include, but are not limited to, activities which add posttranslational modifications to proteins, such as phosphorylation, glycosylation, acylation, acetylation, proteolysis, methylation, and ubiquitination, as well as activities which remove posttranslational modifications or degrade nucleic acids or proteins.

In one embodiment, the genome is from a first cell and the signal transduction protein is from a second cell. In one embodiment, the method includes the step, prior to step (a), of contacting the signal transduction protein with the genomic DNA. In one embodiment, the signaling pathway component is contacted with the genome ex vivo by contacting (i) an extract comprising the signaling pathway component; and (ii) an extract comprising the genome. In one embodiment, the signaling pathway component is a recombinant protein. In one embodiment, the signal transduction protein is a naturally-occurring protein. In one embodiment, the signal transduction protein is not a transcriptional activator, transcription factor or histone. In one embodiment, the first cell and the second cells are from different species.

Another aspect of the invention provides improved cross-linking methods for isolating DNA fragments to which a signal transduction protein is bound. This method, in turn, is useful, for example, for performing genome-wide location analysis. In one embodiment, the signal transduction protein is cross-linked to genomic DNA in a solution comprising paraformaldehyde. Applicants have made an unexpected discovery that paraformaldehyde is superior to formaldehyde for crosslinking at least some proteins to genomic DNA. In one embodiment, cells are cross-linked in a solution that includes from about 0.1% to about 10% paraformaldehyde, such as from about 0.5 to about 2% paraformaldehyde, or about 1% paraformaldehyde. Fixation may be performed from about 10 minutes to about 10 hours, such as from about 1 to about 4 hours. In some embodiments, the paraformaldehyde molecules have predominantly one molecular weight, such as about 600 Daltons. For example, at least 50%, 60%, 70%, 80%, 90% or more of the molecules may have a particular molecular weight or be within a particular weight range. In other embodiments, the paraformaldehyde molecules in the solution have two, three, four, five or more predominant molecular weights. For example, at least 50%, 60%, 70%, 80%, 90% or more of the molecules may collectively have a particular set of molecular weights or be within a particular set of weight ranges. In some embodiments, the molecular weights are substantially uniformly distributed over a range, such as from about 200 to about 1000 Daltons. Using a mixture of molecular weight paraformaldehyde molecules may be useful to maximize the cross-links that are generated between the polypeptide and the DNA.

In another embodiment, the cells are cross-linked in a solution which includes a mixture of paraformaldehyde and a second cross-linking agent. In one embodiment, the second cross-linking agent is formaldehyde. In another embodiment, the second cross-linking agent is selected from glutaraldehyde, divinyl sulfone, a polyanhydride, a polyaldehyde, a polyhydric alcohol, carbodiimide, epichlorohydrin, ethylene glycol, butanediol diglycidylether, diglycidylether, polyglycerol polyglycidylether, polyethylene glycol diglycidylether, polypropylene glycol diglycidylether, or a bis- or poly-epoxy cross-linker. In one embodiment, the second agent is a poly (alkylaldehyde). In one embodiment, the solution includes paraformaldehyde and a second cross-linking agent at a molar ratio of between about 20:1, 10:1, 5:1, 4:1, 3:1, 2:1, 1:1, 1:2, 1:3, 1:4, 1:5, 1:10, or 1:20, or any intermediate ratio thereof.

The above embodiments may be employed using proteins other than signal transduction proteins. For example, they may be employed with any protein for which Chip-on-Chip analysis is used. Chip-on-Chip analysis methods include those described in U.S. Pat. No. 6,410,243; the disclosure of which is herein incorporated by reference. The invention provides variations and improvements of previously described methods for genome-wide location analysis, wherein paraformaldehyde is used, e.g., as described herein.

Methods of Identifying Chromosome Regions

One aspect of the invention provides methods for identifying genes that are regulated by a signal transduction pathway based on the physical association between a signal transduction protein and the genomic DNA that includes the transcribed regions of the gene or its regulatory regions e.g. its promoter.

In one embodiment of the methods described herein, the signal transduction protein is covalently crosslinked to the genomic DNA prior to fragmenting the genomic DNA. There are a variety of methods which can be used to link a signal transduction protein (or other protein) to genomic DNA. In one embodiment of the methods described herein, the crosslinking is formaldehyde cross-linking (Solomon, M J. and Varshavsky, A., Proc. Natl. Sci. USA 82:6470-6474; Orlando, V., TIBS, 25:99-104). In another embodiment, the crosslinking is achieved using paraformaldehyde, e.g., as described herein. UV light may also be used (Pashev et al. *Trends Biochem Sci.* 1991; 16(9):323-6; Zhang L et al. *Biochem Biophys Res Commun.* 2004; 322(3):705-11).

In one embodiment of the methods described herein where the signal transduction protein is covalently cross-linked to the genomic DNA prior to fragmenting the genomic DNA of the cell, separating the DNA fragment from the signal transduction protein includes the step of reversing the crosslink. In a specific embodiment, this method includes the steps of (i) isolating a DNA fragment to which the signal transduction protein is bound from the mixture produced in (a); and (ii) separating (1) the DNA fragment from (2) the signal transduction protein. In a specific embodiment, separating the DNA fragment from the signal transduction protein to which it is bound includes the steps of removing the crosslink between the DNA fragment and the signal transduction protein and removing the signal transduction protein from the DNA fragment. This step may be accomplished, for example, by degrading the signal transduction protein. In one embodiment, a protease (such as proteinase K) is used to degrade the signal transduction protein.

Suitable non-limiting methods for purifying the DNA fragment include column chromatography (U.S. Pat. No. 5,707,812), the use of hydroxylated silica polymers (U.S. Pat. No. 5,693,785), rehydrated silica gel (U.S. Pat. No. 4,923,978), boronated silicates (U.S. Pat. No. 5,674,997), modified glass fiber membranes (U.S. Pat. Nos. 5,650,506; 5,438,127), fluorinated adsorbents (U.S. Pat. No. 5,625,054; U.S. Pat. No. 5,438,129), diatomaceous earth (U.S. Pat. No. 5,075,430), dialysis (U.S. Pat. No. 4,921,952), gel polymers (U.S. Pat. No. 5,106,966) and the use of chaotropic compounds with DNA-binding reagents (U.S. Pat. No. 5,234,809). Commercially available DNA isolation and purification kits are also available from several sources including Stratagene (CLEARCUT Miniprep Kit), and Life Technologies (GLASSMAX DNA Isolation Systems).

In some embodiments of the methods described herein, the genomic DNA is fragmented mechanically, such as by hydrodynamic shearing or sonication. Mechanical fragmentation can occur by any method known in the art, including shearing of DNA by passing it through the narrow capillary or orifice (Oefner et al., 1996, *Nucleic Acids Res.;* 24(20):3879-86; Thorstenson et al., 1998, *Genome Res.;* 8(8):848-55), sonicating the DNA, such as by ultrasound (Bankier, 1993, *Methods Mol. Biol.;* 23:47-50, or grinding in cell homogenizers (Rodriguez L V. *Arch Biochem Biophys.* 1980; 200(1): 116-29). Mechanical fragmentation results, in certain embodiments, in double strand breaks within the DNA molecule. Sonication may also be performed using any convenient approach, e.g., with a Up sonicator, such as a multi-tip sonicator, or using acoustic soundwaves. A Microplate Sonicator® (Misonix Inc.) may be used to partially fragment the DNA. Such a device is described in U.S. Patent Publication No. 2002/0068872. Another acoustic-based system that may be used to fragment DNA is described in U.S. Pat. No. 6,719,449, manufactured by Covaris Inc. U.S. Pat. No. 6,235,501 describes a mechanical method of producing high molecular weight DNA fragments by application of rapidly oscillating reciprocal mechanical energy to cells in the presence of a liquid medium in a closed container, which may be used to mechanically fragment the DNA.

Genomic sequences may be amplified prior to or after a fragmentation step. In one embodiment, an amplification step is used which does not substantially reduce the complexity of the initial source of nucleic acids, e.g., genomic DNA is obtained without a pre-selection step or genomic DNA which has been enriched by selecting for fragments which bind to a signal transduction protein, and amplification employs a random set of primers or primers whose complements occur at a desired frequency throughout the genome or whose complements are engineered to be included in a plurality (e.g., all) genomic fragments obtained from a sample (e.g., such as linkers ligated to the ends of genomic fragments).

However, in other embodiments, amplification can be performed which enriches for certain types of sequences, e.g., sequences which contains a consensus binding site for a signal transduction protein.

Methods for amplifying nucleic sequences can vary. In one aspect, nucleic acids are amplified using an isothermal amplification technique. In another aspect, nucleic acids are amplified using a strand displacement technique, such as multiple strand displacement. In a further aspect, the nucleic acid is amplified using random primers, degenerate primers and/or primers which bind to a constant sequence ligated to ends of genomic fragments in a sample. In certain aspects, amplified isolated DNA fragments are labeled, e.g., labeled probes are generated from the fragments by labeling an amplification product of the fragments.

In one embodiment, the chromatin fragments bound by the signal transduction protein (e.g. a transcriptional regulator or a histone) are isolated using chromatin immunoprecipitation (ChIP). Briefly, this technique involves the use of a specific antibody to immunoprecipitate chromatin complexes comprising the corresponding antigen i.e. the signal transduction protein, and examination of the nucleotide sequences present in the immunoprecipitate. Immunoprecipitation of a particular sequence by the antibody is indicative of interaction of the antigen with that sequence. See, for example, O'Neill et al. in *Methods in Enzymology, Vol.* 274, Academic Press, San Diego, 1999, pp. 189-197; Kuo et al. (1999) Method 19:425-433; and Ausubel et al., supra, Chapter 21. Accordingly, in one embodiment, the DNA fragment bound by the signal transduction protein is identified using an antibody which binds to the signal transduction protein.

In one embodiment, the chromatin immunoprecipitation technique is applied as follows, in the context of a MAPK. Cells which express the MAPK are treated with an agent that cross-links the MAPK to chromatin, such as with paraformaldehyde and/or formaldehyde treatment or ultraviolet irradiation. Subsequent to cross-linking, cellular nucleic acid is isolated, fragmented and incubated in the presence of an antibody directed against the MAPK. Antibody-antigen complexes are precipitated, cross-links are reversed (for example, formaldehyde-induced DNA-protein cross-links can be reversed by heating) so that the sequence content of the immunoprecipitated DNA is tested for the presence of one or more specific sequences. The antibody may bind directly to an epitope on the MAPK or it may bind to an affinity tag on the MAPK, such as a myc tag recognized by an anti-Myc antibody (Santa Cruz Biotechnology, sc-764). A non-antibody agent with affinity for the signal transduction protein, or for a tag fused to it, may be used in place of the antibody. For example, if the MAPK comprises a six-histidine tag, complexes may be isolated by affinity chromatography to a metal ion chelator, e.g., nickel-containing sepharose, etc. Additional variations on ChIP methods may be found in Kurdistani et al. Methods. 2003 31(11):90-5; O'Neill et al. Methods. 2003, 3 1(11):76-82; Spencer et al., Methods. 2003; 3 1(1): 67-75; and Orlando et al. Methods 11: 205-214 (1997). Other binding agents such as aptamers could also be used.

In one embodiment of the methods described herein, DNA fragments from a control immunoprecipitaton reaction are used in place of the isolated chromatin as a control. For example, an antibody that does not react with a MAPK being tested may be used in a chromatin IP procedure to isolate control chromatin, which can then be compared to the chromatin isolated using an antibody that binds to the MAPK. In certain embodiments, the antibody that does not bind to the MAPK being tested also does not react with other MAPKs.

The identification of genomic regions from the isolated DNA fragments may be achieved by generating DNA or RNA probes from the fragment (such as by using the isolated DNA fragments as templates for DNA or RNA synthesis), and hybridizing them to a DNA microarray, such as a DNA microarray comprising immobilized nucleic acids complementary to regions of the genome. In one embodiment, the probes are labeled to facilitate their detection. The probes may be labeled during their synthesis, such as by synthesizing them in the presence of labeled nucleotides, or they may be labeled subsequent to their synthesis. In other embodiments, detection agents may be used to label the DNA/RNA probes once they have hybridized to a nucleic acid, e.g., DNA, microarray. Such detection agents include antibodies, antibody fragments, and dendrimers among others.

In one embodiment, labeled probes are generated by using the DNA fragments as templates for DNA or RNA synthesis by polymerases, such as by using the polymerase chain reaction. DNA synthesis may be primed using random primers. Random priming is described in U.S. Pat. Nos. 5,106,727 and 5,043,272. In some embodiments, the labeled probes are generated using ligation-mediated polymerase chain reaction (LM-PCR). LM-PCR is described, for example, in U.S. Application No. 2003/0143599. Other methods for DNA labeling include direct labeling, 77 RNA polymerase amplification, aminoallyl labeling and hapten-antibody enzymatic labeling. In one embodiment, the labeled probes comprise a fluorescent molecule, such as Cy3 or Cy5 dyes. In another embodiment, the labeled probes include semiconducting nanocrystals, also known as quantum dots. Quantum dots are described in U.S. Publication Nos. 2003/0087239 and 2002/0028457, and in international PCT publication No. WO01/61040.

Extension products that are produced as described above may be labeled in the present methods. As such, the reagents employed in the subject primer extension reactions may include a labeling reagent, where the labeling reagent may be the primer or a labeled nucleotide, which may be labeled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, such as a fluorescent label, where the labeling reagent employed in such embodiments is a fluorescently tagged nucleotide(s), e.g., dCTP. Fluorescent moieties which may be used to tag nucleotides for producing labeled nucleic acids include, but are not limited to: fluorescein, the cyanine dyes, such as Cy3, Cy5, Alexa 555, Bodipy 630/650, and the like. Other labels may also be employed as are known in the art.

When control probes are used, the control probes may be labeled with the same label or different labels as the experimental probes, depending on the actual assay protocol employed. For example, where each set of probes is to be contacted with different but identical arrays, each set of probes may carry the same label. Alternatively, where both sets are to be simultaneously contacted with a single array of immobilized oligonucleotide features, the sets may be differentially labeled.

In some embodiments, the nucleic acid probes are not labeled. For example, in certain embodiments, binding events on the surface of a substrate (such as an oligonucleotide microarray) may be detected by means other than by detection of a labeled nucleic acids, such as by change in conformation of a conformationally labeled immobilized oligonucleotide, detection of electrical signals caused by binding events on the substrate surface, etc.

In one embodiment, identifying a region of the genome of the cell which is complementary to the isolated DNA fragments includes combining the probe(s) with one or more sets of distinct oligonucleotide features bound to a surface of a solid support under conditions such that nucleic acid hybridization to the surface immobilized features can occur, wherein the distinct oligonucleotide features are each complementary to a region of the genome, under conditions in which specific hybridization between the probe and the oligonucleotide features can occur, and detecting said hybridization, wherein hybridization between the probe and the oligonucleotide features relative to a suitable control indicates that the signal transduction protein is bound to the region of the genome to which the sequence of the oligonucleotide features is complementary. "Specific hybridization" refers in certain embodiments to hybridization occurring under stringent conditions.

The experimental and control probes can be contacted to the surface immobilized features either simultaneously or serially. In certain embodiments the compositions are contacted with the plurality of surface immobilized features, e.g., the array of distinct oligonucleotides of different sequence, simultaneously. Depending on how the collections or populations are labeled, the collections or populations may be contacted with the same array or different arrays, where, when the collections or populations are contacted with different arrays, the different arrays are substantially, if not completely, identical to each other in terms of feature content and organization.

An oligonucleotide bound to a surface of a solid support refers to an oligonucleotide or mimetic thereof, e.g., PNA or LNA molecule, that is immobilized on a surface of a solid substrate in a feature or spot, where the substrate can have a variety of configurations, e.g., a sheet, bead, or other structure. In certain embodiments, the collections of features of oligonucleotides employed herein are present on a surface of the same planar support, e.g., in the form of an array.

Arrays refer to an ordered array presented for binding to nucleic acids and the like, and include microarrays. Arrays, as described in greater detail below, are generally made up of a plurality of distinct or different features. The term "feature" is used interchangeably herein with the terms: "features," "feature elements," "spots," "addressable regions," "regions of different moieties," "surface or substrate immobilized elements" and "array elements," where each feature is made up of oligonucleotides bound to a surface of a solid support, also referred to as substrate immobilized nucleic acids. An "array," includes any one-dimensional, two-dimensional or substantially two-dimensional (as well as a three-dimensional) arrangement of addressable regions (i.e., features, e.g., in the form of spots) bearing nucleic acids, particularly oligonucleotides or synthetic mimetics thereof (i.e., the oligonucleotides defined above), and the like. Where the arrays are arrays of nucleic acids, the nucleic acids may be adsorbed, physisorbed, chemisorbed, or covalently attached to the arrays at any point or points along the nucleic acid chain. Exemplary arrays are described in U.S. Patent Pub No. 2004/0191813.

Any given substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100μ$^2$, or even smaller. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

The number of nucleic acid features of an array may vary, where the number of features present on the surface of the array may be at least 2, 5, or 10 or more such as at least 20 and including at least 50, where the number may be as high as about 100, as about 500, as about 1000, as about 5000, as about 10000 or higher. In representative embodiments, the subject arrays have a density ranging from about 100 to about 100,000 features/cm$^2$, such as from about 500 to about 20,000 features/cm$^2$, including from about 1000 to about 20,000 features/cm$^2$. In representative embodiments, the density of single-stranded nucleic acids within a given feature is selected to optimize efficiency of the RNA polymerase. In certain of these representative embodiments, the density of the single-stranded nucleic acids may range from about 10-3 to about 1 pmol/mm$^2$, such as from about 10-2 to about 0.1 pmol/mm$^2$, including from about 5×10$^{-2}$ to about 0.1 pmol/mm$^2$.

In certain aspects, even at high density (e.g., about 10,000 features/cm$^2$ or higher, such as about 50,000 features/cm$^2$ or higher, including about 100,000 features/cm$^2$ or higher, there are inter-feature areas between the majority of features, substantially free of oligonucleotides.

Additionally, the sequence of nucleotides in a given feature may vary based on a particular synthesis reaction. For example, while the majority of oligonucleotides in a feature may be 60 nucleotides long, (i.e., 60-mers), some may be less than 60-mers but otherwise include subsequences of the 60-mer sequence. However, in one aspect, about 75% or more, such as about 80% or more, including about 90% or more, such as about 95% (by number) or more of the oligonucleotides of a feature include identical sequences (e.g., sequences of identical base composition and length).

In those embodiments where an array includes two more features immobilized on the same surface of a solid support, the array may be referred to as addressable. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces.

In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

In one embodiment, an array is synthesized using a method as described in U.S. Ser. No. 10/813,467, the entirety of which is incorporated by reference herein.

In some embodiments, previously identified regions from a particular chromosomal region of interest are used as array elements. Such regions are becoming available as a result of rapid progress of the worldwide initiative in genomics. In certain embodiments, the array can include features made up of surface immobilized oligonucleotides which "tile" a particular region (which have been identified in a previous assay), by which is meant that the features correspond to region of interest as well as genomic sequences found at defined intervals on either side of the particular region of interest, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses tiled arrays tailored to the initially identified region to further assay the region at a higher resolution, e.g., in an iterative protocol. Accordingly, the subject methods include at least two iterations, where the first iteration of the subject methods identifies a region of interest, and the one or more subsequent iterations assay the region with sets of tiled surface immobilized features, e.g., of increasing or alternate resolution.

Of interest are both coding and non-coding genomic regions, (as well as regions that are transcribed but not translated), where by coding region is meant a region of one or more exons that is transcribed into an mRNA product and from there translated into a protein product, while by non-coding region is meant any sequences outside of the exon regions, where such regions may include regulatory sequences, e.g., promoters, enhancers, introns, inter-genic regions, etc. In certain embodiments, one can have at least some of the features directed to non-coding regions and others directed to coding regions. In certain embodiments, one can have all of the features directed to non-coding sequences. In certain embodiments, one can have all of the features directed to, i.e., corresponding to, coding sequences.

In some embodiments, adjacent tiled oligonucleotide features may be spaced at about at least 10 bp, 25 bp, 50 bp, 100 bp, 150 bp, 200 bp, 300 bp, 500 bp, 750 bp, 11 kb, 2 kb, 3 kb, 4 kb, 5 kb, 6 kb, 7 kb, 8 kb, 9 kb, 10 kb or 20 kb relative to their positions in the genome.

In other embodiments, adjacent tiled oligonucleotide features may be spaced at about at most 10 bp, 25 bp, 50 bp, 100 bp, 150 bp, 200 bp, 300 bp, 500 bp, 750 bp, 1 kb, 2 kb, 3 kb, 4 kb, 5 kb, 6 kb, 7 kb, 8 kb, 9 kb, 10 kb or 20 kb relative to their positions in the genome.

In one embodiment, the oligonucleotide features include a nucleic acid having a length ranging from about 10 to about 200 nt, including from about 10 or about 20 nt to about 100 nt, where in certain embodiments the immobilized nucleic acids range in length from about 50 to about 90 nt or about 50 to about 80 nt, such as from about 50 to about 70 nt. In one embodiment, the nucleic acid has a length of about 60 nucleotides.

In one embodiment, the oligonucleotide features bound to a surface of a solid support include sequences representative of locations distributed across at least a portion of a genome. In one embodiment, the oligonucleotide features have target complements spaced (uniformly or non-uniformly) throughout the genome. In one aspect, a probe set includes probe sequences representing 47 different loci, one on each p and q arm of the 23 human chromosomes plus one locus on the Y-chromosome. In another aspect, the probe set comprises probe sequences which include repetitive sequences (e.g., such as Alu sequences, centromeric sequences, telomere sequences, LINE sequences, SINE sequences and the like). In one embodiment, the oligonucleotide features bound to a surface of a solid support samples the portion of the genome at every 20, about every 10, about every 5, about every 4, about every 3, about every 2, about every 1, about every 0.5 kb or greater frequency. In one embodiment, the portion of the genome includes about 20%, about 30%, about 40%, about 50%, about 60%, about 70%, about 80%, about 90%, about 95% or more of (i) total genomic DNA; (ii) open-reading frames; (iii) promoter regions; (iv) genic regions; or (v) chromosomes. In one embodiment, the portion of the genome includes about 1 Mb, about 2 Mb, about 3 Mb, about 4 Mb, about 5 Mb, about 10 Mb, about 15 Mb, about 25 Mb, about 50 Mb, about 100 Mb, about 200 Mb, about 500 Mb, about 1000 Mb, about 2000 Mb or about 3000 Mb or more of genomic sequence. For example, 5,000 oligonucleotide features of about 60 nucleotides each may be used to tile a 5 Mb portion of a chromosome at every about 1 kb.

In one embodiment, about 20%, about 30%, about 40%, about 50%, about 60%, about 70%, about 80%, about 90% or about 95% (by number) or more of the oligonucleotide features correspond to non-coding genomic regions. In one embodiment, about 20%, about 30%, about 40%, about 50%, about 60%, about 70%, about 80%, about 90% or about 95% (by number) or more of the oligonucleotide features correspond to non-promoter regions: In one embodiment, about 20%, about 30%, about 40%, about 50%, about 60%, about 70%, about 80%, about 90% or about 95% (by number) or more of the oligonucleotide features do not include entire reading frames or entire exons or both.

Arrays can be fabricated using drop deposition from pulsejets of either nucleic acid precursor units (such as monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

In certain embodiments of particular interest, in situ prepared arrays are employed. In situ prepared oligonucleotide arrays, e.g., nucleic acid arrays, may be characterized by having surface properties of the substrate that differ significantly between the feature and inter-feature areas. Specifically, such arrays may have high surface energy, hydrophilic features and hydrophobic, low surface energy hydrophobic inter-feature regions. Whether a given region, e.g., feature or inter-feature region, of a substrate has a high or low surface energy can be readily determined by determining the regions "contact angle" with water, as known in the art and further described in copending application Ser. No. 10/449,838, the disclosure of which is herein incorporated by reference. Other features of in situ prepared arrays that make such array formats of particular interest in certain embodiments of the present invention include, but are not limited to: feature density, oligonucleotide density within each feature, feature uniformity, low intra-feature background, low inter-feature background, e.g., due to hydrophobia interfeature regions, fidelity of oligonucleotide features making up the individual features, array/feature reproducibility, and the like. The above benefits of in situ produced arrays assist in maintaining adequate sensitivity while operating under stringency conditions required to accommodate highly complex samples.

Generally, nucleic acid hybridizations between the probes and the arrays include the following major steps: (1) provision of array of surface immobilized nucleic acids or features; (2) optionally pre-hybridization treatment to increase accessibility of features, and to reduce nonspecific binding; (3) hybridization of the nucleic acid probes to the features on the solid surface, typically under high-stringency conditions; (4) post-hybridization washes to remove probes not bound in the hybridization; and (5) detection of the hybridized probes. The reagents used in each of these steps and their conditions for use may vary depending on the particular application.

As indicated previously, hybridization is carried out under suitable hybridization conditions, which may vary in stringency as desired. In certain embodiments, highly-stringent hybridization conditions may be employed. The term "highly-stringent hybridization conditions" as used herein refers to conditions that are compatible to produce nucleic acid binding complexes on an array surface between complementary binding members, i.e., between immobilized features and complementary solution phase nucleic acids in a sample. High-stringency assay conditions that may be employed in these embodiments are provided above.

The hybridization step may include agitation of the immobilized features and the sample of solution phase nucleic acids, where the agitation may be accomplished using any convenient protocol, e.g., shaking, rotating, spinning, and the like. Following hybridization, the surface of immobilized nucleic acids is typically washed to remove unbound nucleic acids. Washing may be performed using any convenient washing protocol, where the washing conditions are typically stringent, as described above.

Following hybridization and washing, as described above, the hybridization of the probes to the array is then detected using standard techniques so that the surface of immobilized features, e.g., array, is read. Reading of the resultant hybridized array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER available from Agilent Technologies, Santa Clara, Calif. Other suitable devices and methods are described in U.S. patent application Ser. No. 09/846, 125 "Reading Multi-Featured Arrays" by Dorsel et al.; and U.S. Pat. No. 6,406,849, which references are incorporated herein by reference.

Arrays, however, may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere).

In the case of indirect labeling, subsequent treatment of the array with the appropriate reagents may be employed to enable reading of the array. Some methods of detection, such as surface plasmon resonance, do not require any labeling of the nucleic acids, and are suitable for some embodiments. In some embodiments, detecting the hybridization between the labeled/unlabeled probes and the nucleic acids complementary to the genome is facilitated by contacting the complexes between the labeled or unlabeled probe and the nucleic acid on the array with a detection agent, wherein the amount of detection agent that binds to the complex is indicative of the level of hybridization. In one embodiment, the detection agent comprises an antibody or fragment thereof. In another embodiment, the detection agent comprises a dendrimer. The use of dendrimers for the detection of microarray hybridization has been described in U.S. Pat. Pub. Nos. 2002/0051981 and 2002/0072060, hereby incorporated by reference in their entirety. In another embodiment, the detection agent binds to a double stranded nucleic acid selected from the group consisting of a DNA-DNA, DNA-RNA or RNA-RNA double stranded-nucleic acids.

Results from the reading or evaluating may be raw results (such as fluorescence intensity readings for each feature in one or more color channels) or may be processed results, such as obtained by subtracting a background measurement, or by rejecting a reading for a feature which is below a predetermined threshold and/or forming conclusions based on the pattern read from the array (such as whether or not a particular feature sequence may have been present in the sample, or whether or not a pattern indicates a particular condition of an organism from which the sample came).

DNA microarray and methods of analyzing data from microarrays are well-described in the art, including in DNA Microarrays: A Molecular Cloning Manual, ed by Bowtel and Sambrook (Cold Spring Harbor Laboratory Press, 2002); Microarrays for an Integrative Genomics by Kohana (MIT Press, 2002); A Biologist's Guide to Analysis of DNA Microarray Data, by Knudsen (Wiley, John & Sons, Incorporated, 2002); and DNA Microarrays: A Practical Approach, Vol. 205 by Schema (Oxford University Press, 1999); and Methods of Microarray Data Analysis II, ed by Lin et al. (Kluwer Academic Publishers, 2002), hereby incorporated by reference in their entirety.

In certain embodiments of the methods described herein, one or more steps are performed in different locations. In one embodiment, the fragments to which the signal transduction protein binds are isolated in a first location, while hybridization of the probes to an array is performed in a second location. An optional step of synthesizing probes from the fragments may be performed at either location. When two locations are used, the methods include, in some embodiments, the transport of DNA fragments or probes generated therefrom from the first location to the second location. In one embodiment, the first location is remote to the second location. A remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. In one embodiment, two locations that are remote relative to each other are at least 1, 2, 3, 4, 5, 10, 20, 50, 100, 200, 500, 1000, 2000 or 5000 km apart. In another embodiment, the two locations are in different countries, where one of the two countries is the United States.

Some specific embodiments of the methods described herein where steps are performed in two or more locations comprise one or more steps of communicating information between the two locations. "Communicating" information means transmitting the data representing that information, such as in the form of electrical signals, over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

In one specific embodiment, the methods include one or more data transmission steps between the locations. In one embodiment, the data transmission step occurs via an electronic communication link, such as the Internet. In one embodiment, the data transmission step from the first to the second location includes experimental parameter data, wherein the experimental parameter data comprises data selected from: (a) the phylogenetic species of the genome; (b) clinical data from the organism from which the genome was derived; and (c) a microarray to which the labeled probes are to be hybridized.

In some embodiments, the data transmission step from the second location to the first location includes data transmission to intermediate locations. In one embodiment, the method comprises one or more data transmission substeps from the second location to one or more intermediate locations and one or more data transmission substeps from one or more intermediate locations to the first location, wherein the intermediate locations are remote to both the first and second locations. In another embodiment, the method includes a data transmission step in which a result from identifying regions of a genome is transmitted from the second location to the first location.

The signal transduction protein may be native to the cell, or it may be a recombinant protein. By native it is meant that the signal transduction protein occurs naturally in the cell. In some embodiments, the signal transduction protein is from a species which is different from that of the genome. In some embodiments, the signal transduction protein is a viral protein. In such embodiments, a cell having the genome may be contacted with the virus and chromatin extracted from the infected cell after allowing sufficient time for the viral proteins to be expressed. In some embodiments, a recombinant signal transduction protein may have missense mutations, truncations, or inserted sequences or entire domains from other naturally-occurring proteins. A tagged signal transduction protein may be used in some embodiments, especially when the tag facilitates its immunoprecipitation.

In certain embodiments of the invention, the signal transduction pathway is a cAMP-dependent protein kinase (PKA) pathway, a two-component system ortholog signaling pathway, a MAPK signaling pathway, a Wnt signaling pathway, a Notch signaling pathway, a Hedgehog signaling pathway, a TGF-beta signaling pathway, a Toll-like receptor signaling pathway, a JakSTAT signaling pathway, a Calcium signaling pathway, a phosphatidylinositol signaling system, an insulin signaling pathway, an adipocytokine signaling pathway, an integrin signaling pathway, a PPAR signaling pathway, a cytokine signaling pathway, a T cell receptor signaling pathway or a B cell receptor signaling pathway.

The methods described herein may be applied to signal transduction proteins that have been causally implicated in a disease. Examples of diseases and signal transduction proteins which cause them may be found in the scientific and medical literature by one skilled in the art, including in Medical Genetics, L. V. Jorde et al., Elsevier Science 2003, and Principles of Internal Medicine, 15th edition, ed by Braunwald et al., McGraw-Hill, 2001; American Medical Association Complete Medical Encyclopedia (Random House, Incorporated, 2003); and The Mosby Medical Encyclopedia, ed by Glanze (Plume, 1991). In some embodiments, the disorder is characterized by impaired function of at least one of the following organs or tissues: brain, spinal cord, heart, arteries, esophagus, stomach, small intestine, large intestine, liver, pancreas, lungs, kidney, urinary tract, ovaries, breasts, uterus, testis, penis, colon, prostate, bone, scalp, muscle, cartilage, thyroid gland, adrenal gland, pituitary, bone marrow, blood, thymus, spleen, lymph nodes, skin, eye, ear, nose, teeth or tongue.

In some embodiments of the methods described herein, the cell has been treated with an agent, such as compound or a drug, prior to the fragmenting of genomic DNA and in certain embodiments while the cell is alive. Agents of interest include, but are not limited to, those which bind to and/or regulate receptors which trigger the signal transduction cascade. These may include agents which bind to transmembrane GPCRs or RTKs. In some embodiments, the genes that are bound by a signal transduction protein are determined both in a cell that is contacted with an agent and in a cell that is not contacted with the agent, or that is contacted with a different amount of the agent. Such methods may be used to identify compounds that alter the types of genes and/or the extent the genes are regulated by the signal transduction pathway.

In some embodiments, the agent or drug includes a small molecule drug, an antisense nucleic acid, an antibody, a peptide, a ligand, a fatty acid, a hormone or a metabolite. Exemplary compounds that may be used as agents (e.g., a single compound, a combination of two or more compounds, a library of compounds) include nucleic acids, peptides, polypeptides, peptidomimetics, antibodies, antisense oligonucleotides, RNAI constructs (including siRNAs), ribozymes, chemical compounds, and small organic molecules.

Compounds may be screened individually, in combination, or as a library of compounds. The assays described herein may also be used to screen a library of compounds to test the activity of each library member on the DNA-binding properties of signal transduction protein. Library members may be produced and/or otherwise generated or collected by any suitable mechanism, including chemical synthesis in vitro, enzymatic synthesis in vitro, and/or biosynthesis in a cell or organism. Chemically and/or enzymatically synthesized libraries may include libraries of compounds, such as synthetic oligonucleotides (DNA, RNA, peptide nucleic acids, and/or mixtures or modified derivatives thereof), small molecules (about 100 Da to 10 KDa), peptides, carbohydrates, lipids, and/or so on. Such chemically and/or enzymatically synthesized libraries may be formed by directed synthesis of individual library members, combinatorial synthesis of sets of library members, and/or random synthetic approaches. Library members produced by biosynthesis may include libraries of plasmids, complementary DNAs, genomic DNAs, RNAs, viruses, phages, cells, proteins, peptides, carbohydrates, lipids, extracellular matrices, cell lysates, cell mixtures, and/or materials secreted from cells, among others. Library members may be contact arrays of cell populations singly or as groups/pools of two or more members.

In one embodiment, fragmenting the genomic DNA includes fragmenting the genomic DNA of a population of cells. In one embodiment of the methods described herein, the population of cells includes about $10^8$, about $10^7$, about $10^6$, about $10^5$, about $10^4$, about $10^3$ or about $10^2$ or fewer cells. In some embodiments, the population of cells includes about $10^8$, about $10^7$, about $10^6$, about $10^5$, about $10^4$, about $10^3$ or about $10^2$ or fewer cells which express the signal transduction protein, but also includes cells which do not express the signal transduction protein. In one embodiment, the cell population is a population that has been isolated using fluorescent-activated cell-sorting (FACS).

In one embodiment of the methods described herein, the chromatin is from primary cells. Primary cells are isolated from an organism and have undergone minimum passaging in vitro, and thus maintain most of the phenotypic characteristics of cells in the organism. In a specific embodiment, the primary cells are primary cells that have doubled less than ten times ex vivo.

In some embodiments, the chromatin is derived from transplant-grade tissue or freshly isolated tissue. In some embodiments, the cell is derived from a tissue biopsy, such as from a subject afflicted with, or suspected of being afflicted with, a disorder.

The cell type from which the chromatin is obtained may be any cell type. The cell may be an eukaryotic cell or a prokaryotic cell. Eukaryotic cells includes those from metazoans and those from single-celled organisms such as yeast. In some preferred embodiments, the cell is a mammalian cell, such as a cell from a rodent, a primate or a human. The cell may be a wild-type cell or a cell that has been genetically modified by recombinant means or by exposure to mutagens. The cell may be a transformed cell or an immortalized cell. In some embodiments, the cell is from an organism afflicted by a disease. In some embodiments, the cell comprises a genetic mutation that results in disease, such as in a hyperplastic condition.

In certain embodiments of the methods described herein, the cell populations are contained within wells of multi-well plates to facilitate parallel handling of cells and reagents. In specific embodiments, the multi-well plate has 24, 48, 96 or 384 wells. Standard 96 well microtiter plates which are 86 mm by 129 mm, with 6 mm diameter wells on a 9 mm pitch, may be used for compatibility with current automated loading and robotic handling systems. The microplate is typically 20 mm by 30 mm, with cell locations that are 100-200 microns in dimension on a pitch of about 500 microns. Methods for making microplates are described in U.S. Pat. No. 6,103,479, incorporated by reference herein in its entirety.

Microplates may consist of coplanar layers of materials to which cells adhere, patterned with materials to which cells will not adhere, or etched 3-dimensional surfaces of similarly patterned materials. For the purpose of the following discussion, the terms "well" and "microwell" refer to a location in an array of any construction to which cells adhere and within which the cells are imaged. Microplates may also include fluid delivery channels in the spaces between the wells. The smaller format of a microplate increases the overall efficiency of the system by minimizing the quantities of the reagents, storage and handling during preparation and the overall movement required for the scanning operation. In addition, the whole area of the microplate can be imaged more efficiently. Multi-well test plates used for isotopic and non-isotopic assays are well known in the art and are exemplified, for example, by those described in U.S. Pat. Nos. 3,111,489; 3,540,856; 3,540,857; 3,540,858; 4,304,865; 4,948,442; and 5,047,215.

Microfluidic devices may also be used at any of the steps of the methods described herein. For example, Chung et al. (2004) *Lab Chip.*; 4(2):141-7 describe a high efficiency DNA extraction microchip was designed to extract DNA from lysed cells using immobilized beads and shaking solution, which allows extraction of as little as $10^3$ cells. Guijt et al. (2003) *Lab Chip;* 3(I):I-4 describes microfluidic devices with accurate temperature control, as might be used to cycle temperature during PCR amplification. Similarly, Liu et al. (2002) *Electrophoresis.*; 23(10): 1531-6 teaches a microfluidic device for performing PCR amplification using as little as 12 nL of sample. Cady et al. (2003) *Biosens Bioelectron.* 30; 19(I):59-66 describes a microfluidic device that may be used to purify DNA.

Another aspect of the invention provides a program product (i.e. software product) for use in a computer device that executes program instructions recorded in a computer-readable medium to analyze data from the array hybridization steps, to transmit array hybridization data from one location to another, or to evaluate genome-wide location data between two or more genomes, such as between a cell exposed to a drug and a control cell.

Another related aspect of the invention provides kits comprising the program product or the computer readable medium, optionally with a computer system. In one embodiment, the program product comprises: a recordable medium; and a plurality of computer-readable instructions executable by the computer device to analyze data from the array hybridization steps, to transmit array hybridization from one location to another, or to evaluate genome-wide location data between two or more genomes. Computer readable media include, but are not limited to, CD-ROM disks (CD-R, CD-RW), DVD-RAM disks, DVD-RW disks, floppy disks and magnetic tape.

A related aspect of the invention provides kits comprising the program products described herein. The kits may also optionally contain paper and/or computer-readable format instructions and/or information, such as, but not limited to, information on DNA microarrays, on tutorials, on experimental procedures, on reagents, on related products, on available experimental data, on using kits, on literature, and on other information. The kits optionally also contain in paper and/or computer-readable format information on minimum hardware requirements and instructions for running and/or installing the software. The kits optionally also include, in a paper and/or computer readable format, information on the manufacturers, warranty information, availability of additional software, technical services information, and purchasing information. The kits optionally include a video or other viewable medium or a link to a viewable format on the internet or a network that depicts the use of the use of the software, and/or use of the kits. The kits also include packaging material such as, but not limited to, styrofoam, foam, plastic, cellophane, shrink wrap, bubble wrap, paper, cardboard, starch peanuts, twist ties, metal clips, metal cans, drierite, glass, and rubber.

The analysis of array hybridization data, as well as the transmission of data steps, can be implemented by the use of one or more computer systems. Computer systems are readily available. The processing that provides the displaying and analysis of image data for example, can be performed on multiple computers or can be performed by a single, integrated computer or any variation thereof. For example, each computer operates under control of a central processor unit (CPU), such as a "Pentium" microprocessor and associated integrated circuit chips, available from Intel Corporation of Santa Clara, Calif., USA. A computer user can input commands and data from a keyboard and display mouse and can view inputs and computer output at a display. The display is typically a video monitor or flat panel display device. The computer also includes a direct access storage device (DASD), such as a fixed hard disk drive. The memory typically includes volatile semiconductor random access memory (RAM).

Each computer typically includes a program product reader that accepts a program product storage device from which the program product reader can read data (and to which it can optionally write data). The program product reader can include, for example, a disk drive, and the program product storage device can include a removable storage medium such as, for example, a magnetic floppy disk, an optical CD-ROM disc, a CD-R disc, a CD-RW disc and a DVD data disc. If desired, computers can be connected so they can communicate with each other, and with other connected computers, over a network. Each computer can communicate with the other connected computers over the network through a network interface that permits communication over a connection between the network and the computer.

The computer operates under control of programming steps that are temporarily stored in the memory in accordance with conventional computer construction. When the programming steps are executed by the CPU, the pertinent system components perform their respective functions. Thus, the programming steps implement the functionality of the system as described above. The programming steps can be received from the DASD, through the program product reader or through the network connection. The storage drive can receive a program product, read programming steps recorded thereon, and transfer the programming steps into the memory for execution by the CPU. As noted above, the program product storage device can include any one of multiple removable media having recorded computer-readable instructions, including magnetic floppy disks and CD-ROM storage discs. Other suitable program product storage devices can include magnetic tape and semiconductor memory chips. In this way, the processing steps necessary for operation can be embodied on a program product.

Alternatively, the program steps can be received into the operating memory over the network. In the network method, the computer receives data including program steps into the memory through the network interface after network communication has been established over the network connection by well known methods understood by those skilled in the art. The computer that implements the client side processing, and the computer that implements the server side processing or any other computer device of the system, can include any conventional computer suitable for implementing the functionality described herein.

In some embodiments, identifying at least one gene regulated by the signal transduction pathway includes determining whether the regions of genomic DNA to which the signal transduction protein binds is part of a gene. In one embodiment, a gene is said to be regulated by the signal transduction pathway if the signal transduction protein binds to a region extending from about 10 kb 5' of the transcription initiation site (or 5 kb, 4 kb, 3 kb, 2 kb or 1 kb) to about 1 kb 3' of the transcription termination site of the gene. In another embodiment, a gene said to be regulated by the signal transduction pathway if the signal transduction protein binds to the promoter of the gene. In another embodiment, a gene said to be regulated by the signal transduction pathway if the signal transduction protein binds to the region of the gene that is transcribed. In another embodiment, a gene said to be regulated by the signal transduction pathway if the signal transduction protein binds to the region of the gene defined by the start and stop codons of the gene.

In certain embodiments, the methods as described above, are employed to generate a profile for a sample of interest. The term "profile" refers to the data representing the identified one or more genes that are bound by the polypeptide of interest. The profile may include data on binding at one or more genomic sites, such as 2 or more, about 5 or more, about 10 or more, about 15 or more, about 20 or more genomic sites. In certain embodiments the sites making up a given profile are 2 or more, about 5 or more, about 10 or more, about 15 or more, about 20 or more genomic sites of genes listed in Tables S2 to S6, infra. After the profile of the sample has been obtained, the profile is compared with a reference or control profile to make an evaluation of the subject from which the sample was obtained. In certain embodiments, the comparison is made with a profile from a sample from an unaffected, normal source. A control dataset may include data that is obtained from a sample that is known to be from a known disorder subject, and therefore may be a positive control profile.

In certain embodiments, the obtained profile is compared to a single control/reference profile to obtain information regarding the phenotype of the subject being assayed. In yet other embodiments, the obtained profile is compared to two or more different reference/control profiles to obtain information regarding the phenotype of the assayed sample. For example, the test profile may be compared to a positive and negative reference profiles to obtain a reliable indication that the subject from which the sample was obtained has insulin resistance or is insulin sensitive.

In one embodiment, a difference value, i.e., a numerical evaluation of the difference a test profile and control profile may be calculated using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference.

Samples can be obtained from the tissues or fluids of an individual, as well as from cell cultures or tissue homogenates. For example, samples can be obtained from whole blood, tissue biopsy, serum, etc. Also included in the term are derivatives and fractions of such cells and fluids. Where cells are analyzed, the number of cells in a sample may be at least about $10^2$, usually at least $10^3$, and may be about $10^4$ or more. The cells may be dissociated, in the case of solid tissues, or tissue sections may be analyzed. Alternatively a lysate of the cells may be prepared.

In certain embodiments, the profile is statistically analyzed to provide an evaluation of the subject for the disorder of interest. In such methods, the profile may be compared to one or more control profiles to provide the evaluation.

The analysis methods may further include input from additional variables, including clinical indicia. Clinical indicia that may be assessed and those data may be combined with the marker expression data to provide a diagnosis for insulin resistance. Such clinical markers include, without limitation: triglycerides, systolic blood pressure, waist size, total cholesterol, gender, age, glucose, insulin, body mass index (BMI), heart rate, diastolic blood pressure, dyslipidemia, cigarette smoking, and the like. Other variables include metabolic measures, genetic information, family history, measures derived from combinations of the above, and other data obtained from patients.

In certain embodiments, the method may include: a) receiving a sample, b) evaluating the sample according to the above-described methods to produce an evaluation of the target disorder, e.g., a diagnosis; and c) communicating the evaluation. The sample may be received from a remote location and/or the diagnosis may be communicated to a remote location, where a "remote location" is meant a second location other than a first location. For example, a remote location could be a different room in the same building (e.g., another laboratory), a different building in the same building complex, or a different location in the same city, state or country, etc. When a cellular sample is indicated as being "received" from a remote location, the cellular sample may be obtained from the remote location or hand-delivered, mailed or couriered from the remote location, for example. "Communicating", in this context, refers to any means of getting that information from one location to the next, whether by physically transporting printed material or computer readable media containing the information (e.g., by mail), or by transmitting the information. If information is transmitted, a digital or analog signal representing the information (e.g., an electromagnetic signal such as a light or electrical signal) is transmitted over a suitable communication channel (for example, a private, public or wireless network). Any convenient means may be employed for transmitting the data, e.g., facsimile, modem, internet, e-mail, etc.

The subject methods further find use in pharmacogenomic applications. In these applications, a subject/host/patient is first diagnosed for the disorder phenotype using a protocol such as the diagnostic protocol described in the preceding section. The subject is then treated using a pharmacological protocol, where the suitability of the protocol for a particular subject/patient is determined using the results of the diagnosis step.

In addition to clinical applications, the methods of the invention are applicable to drug screening applications. For example, the above described profile can be detected before and after a cell is subjected to a given stimulus, so as to identify information regarding how a cell responds to a given stimulus. In yet other embodiments, one can monitor changes in the profile of a cell over time, so as to elucidate how development changes a cell. As such, the subject invention finds use in profiling signal transduction pathways. Yet another application in which the subject invention finds use is in screening, including high throughput screening, for agents that modulate the binding activity of a polypeptide to its recognized DNA sequence, e.g., in screening for agonists and antagonists, including in a high throughput manner. In such assays, a sample is assayed according to the methods described above in the presence and absence of a candidate agent and the effect of the candidate agent on the binding profile of the polypeptide is determined, e.g., by reference to a control. The observed effect or lack thereof is then related to the modulatory capacity of the candidate compound. In this manner, a given agent can be screened for modulatory activity with respect to a polypeptide member of a signal transduction pathway of interest. For example, a potential candidate inhibitory agent can be screened by assaying a sample containing the polypeptide member of the signal transduction pathway of interest according to the subject methods in the presence of the candidate agent and observing the effect of the candidate agent on the obtained results.

The candidate agents screened according to the present methods may be any chemical entity, pharmaceutical, drug, and the like that can be used to treat or prevent a disease, illness, conditions, or disorder of bodily function. Compounds comprise both known and potential therapeutic compounds. A compound can be determined to be therapeutic by screening using the screening methods of the present invention. Examples of test compounds include, but are not limited to peptides, polypeptides, synthetic organic molecules, naturally occurring organic molecules, nucleic acid molecules, and combinations thereof.

The above described screening methods can be used to screen for candidate compounds useful to treat any disorder, such as a disorder associated with the action of the signal transduction pathway.

In one embodiment, the methods are used to identify genes that may be at least in part responsible for a therapeutic effect or an undesired effect (e.g. a side effect) of a first compound such as a pharmacological agent that acts on a signal transduction protein. Such genes (and their encoded) products are targets for the identification of additional pharmacological agents that may either have a similar or antagonistic effect as that of the first compound. The invention therefore provides methods for identifying targets (genes, proteins) for use in additional screening assays to identify agents that behave in a similar or antagonistic manner to a first compound that modulates a signal transduction pathway. In addition the invention provides methods for uncovering the mechanism by which a compound, e.g., a pharmacological agent, exerts a beneficial or deleterious effect on a cell or organism. In one embodiment the invention allows administration of an agent that counteracts a side effect of a pharmacological agent that interacts with a signal transduction protein, wherein the signal transduction protein binds to a gene responsible for the side effect upon exposure to the pharmacological agent.

EXPERIMENTAL

The invention now being generally described, it will be more readily understood by reference to the following examples, which are included merely for purposes of illustration of certain aspects and embodiments of the present invention, and are not intended to limit the invention, as one skilled in the art would recognize from the teachings hereinabove and the following examples, that other DNA microarrays, signaling pathways, cell types, antibodies, ChIP conditions, or data analysis methods, all without limitation, can be employed, without departing from the scope of the invention as claimed.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincoft-Schwartz, Harford, and Yamada, John Wiley and Sons, Inc., New York, 1999; and PCR Protocols, ed; by Bardeft et-al., Humana Press, 2003.

I. MATERIALS AND METHODS

A. Yeast Strains

Strains used in this study are listed in Table S1; most of these were originally generated by the J. Weissman lab (1(S. Ghaemmaghami et al., *Nature* 425, 737-41 (Oct. 16, 2003)), 2(W K. Huh et al., Nature 425, 686-91 (Oct. 16, 2003)), 3(D. K. Pokholok et al., *Cell* 122, 517-27 (Aug. 26, 2005) and 33(C. B. Brachmann et al., *Yeast* 14, 115-32 (Jan. 30, 1998)).

TABLE S1

Yeast strains used in the study

| Strain | Genotype | Reference |
|---|---|---|
| Z989 | MATa his3^1 leu2^0 met5^0 ura3^0 | (33) |
| Z1969 | MATa his3^1 leu2^0 met5^0 ura3^0 HOG1::TAP:HIS3 | (1) |
| Z1966 | MATa his3^1 leu2^0 met5^0 ura3^0 FUS3::TAP:HIS3 | (1) |
| Z1980 | MATa his3^1 leu2^0 met5^0 ura3^0 KSS1::TAP:HIS3 | (1) |
| Z1967 | MATa his3^1 leu2^0 met5^0 ura3^0 STE5::TAP:HIS3 | (1) |
| Z1991 | MATa his3^1 leu2^0 met5^0 ura3^0 SLT2::TAP:HIS3 | (1) |
| Z1975 | MATa his3^1 leu2^0 met5^0 ura3^0 TPK1::TAP:HIS3 | (1) |
| Z1976 | MATa his3^1 leu2^0 met5^0 ura3^0 TPK2::TAP:HIS3 | (1) |
| Z1977 | MATa his3^1 leu2^0 met5^0 ura3^0 TPK3::TAP:HIS3 | (1) |
| Z1962 | MATa his3^1 leu2^0 met5^0 ura3^0 TPK1::TAP:HIS3 gal4^URA3 | This study |
| Z1979 | MATa his3^1 leu2^0 met5^0 ura3^0 SPT16::TAP:HIS3 | (1) |
| Z1318 | MATa ade2-1 trp1-1 can1-100 leu2-3,112 his3-11,15 ura3 GAL+ psu+ RAP1::18myc:TRP1 | (9) |
| Z1346 | MATa ade2-1 trp1-1 can1-100 leu2-3,112 his3-11,15 ura3 GAL+ psu+ ESA1::18myc:TRP1 | (3) |
| Z1998 | MATa his3^1 leu2^0 met5^0 ura3^0 NUP2::TAP:HIS3 | (1) |

The proper tagging of proteins was confirmed by Western blot analysis and by genomic PCR of corresponding loci (data not shown). For gene deletions, the URA3 marker from the plasmid pRS306 was amplified by PCR using primers that are homologous to regions of the gene to be deleted and transformed into yeast. Stable integration of the marker into the gene of interest was selected on URA3-plates and confirmed by genomic PCR analysis.

B. Growth Conditions

Yeast cells were generally grown at 30° C. in rich medium containing 2% glucose (YPD). Replicates were grown as independent cultures. Osmotic stress was induced by addition of NaCl (0.4 M final concentration) for 5 minutes. Pheromone induction was performed by addition of alpha pheromone (5 µg/ml) for 5 min. For growth in a non-fermentable carbon source, complete synthetic medium supplemented with 3% glycerol was used. Oxidative stress was induced by adding hydrogen peroxide (0.4 mM final concentration) and incubation for 20 minutes. Galactose induction was performed by adding galactose (2% final concentration) to a cell culture grown in raffinose-containing medium and incubation for 1 hour.

C. Chromatin Immunoprecipitation and Microarray Hybridization

Chromatin immunoprecipitation and microarray analysis were performed in at least duplicate experiments (biological replicates) as described previously (Pokholok et al., supra). A detailed experimental protocol and additional information on data analysis can be found at the website produced by placing "http://web" before ".wi.mit.edu/young/signaling." Briefly, cells grown in liquid medium were crosslinked for 30 minutes with 1% paraformaldehyde (1% formaldehyde for Tpk1 and Tpk2) at room temperature followed by 90 minutes at 4° C. Cells were collected by centrifugation, washed with ice-cold TBS and disrupted by vortexing in lysis buffer in the presence of glass beads. The chromatin was sonicated to yield an average DNA fragment of 500 bps. The DNA fragments crosslinked to the TAP tagged proteins were enriched by immunoprecipitation with pan mouse IgG beads (Dynal) without specific antibodies.

We also included control immunoprecipitations of lysates from a strain lacking the epitope tag (Z989) grown under the same growth conditions. Additional antibodies were used for Pol II (mouse monoclonal antibody 8WG16) and H3K36 trimethylation (ab 9050 from Abcam). After reversal of the crosslinks and purification, the immunoprecipitated and input DNA was labeled by ligation-mediated PCR with Cy5 and Cy3 fluorescent dyes, respectively. Both pools of labeled DNA were hybridized to a single oligonucleotide DNA microarray (Agilent) containing 44,290 oligonucleotide (60-mer) probes.

The probes cover 12 Mb (85%) of the yeast genome, excluding highly repetitive regions, with an average separation of 266 bp. Images of Cy5 and Cy3 fluorescence intensities were obtained using a GenePix 5000 scanner and were analyzed with GenePix Pro 5.1 software. All microarray data are available from ArrayExpress and from the inventors' website.

D. Genome-Wide ChIP-Chip Data Analysis

Genome-wide location data were normalized, and the ratio of immunoprecipitated to control DNA was determined for each probe (ChIP enrichment). For each array, a confidence value (P value) was calculated for each probe using an error model, and the data from replicates were combined using a weighted average method (Pokholok et al., supra; T. R. Hughes et al., Cell 102, 109-26 (Jul. 7, 2000)). Probes that scored significantly above background were then combined into probe sets of three probes if they passed the following filter: the center probe in the probe set has a single point P value <0.001, one of the flanking probes has a single point P value <0.01 and the three probes combined have a P value <0.001. For binding peaks that typically span over transcribed regions and thus span over several probes, the following filter was used: the center probe in the probe set has a single point P value <0.005, the three probes combined have a P value <0.0001 and one of the flanking probes has a combined P value <0.001. Bound probe sets that overlapped were collapsed into bound regions. For each bound region, the closest ORF was then assigned and the maximum ChIP enrichment identified (see Tables S2-S6 for the results).

E. Expression Data Analysis

Genome-wide expression data under salt conditions (FIG. 1) were from Causton et al. (H. C. Causton et al., Mol Biol Cell 12, 323-37 (February, 2001)) and O'Rourke et al. (S. M. O'Rourke, I. Herskowitz, Mol Biol Cell 15, 532-42 (February, 2004)). The genome-wide expression data in response to pheromone exposure were from Roberts et al. (C. J. Roberts et al., Science 287, 873-80 (Feb. 4, 2000)). The transcriptional rates of yeast genes under normal growth conditions were from Holstege et al. (F. C. Holstege et al., Cell 95, 717-28 (Nov. 25, 1998)). Genes were qualified as increased in transcription if two consecutive time points showed increased transcript levels compared to the control sample.

F. Error Rates

We have estimated that the false positive rate for genome-wide ChIP-Chip experiments carried out under the conditions described here is approximately 1%. Error rates have not been estimated for the expression data. Microarray expression data is the product of both transcription and degradation rates, so genes that are genuinely bound and regulated by a factor may have the change in transcription masked by post-transcriptional events.

G. Comparison Between ChIP-Chip and Gene Expression Data

We did not find that gene occupancy by kinases is always associated with changes in the expression of the bound genes. This is likely to be due to error rates associated with both genome-wide binding data and gene expression data, and due to biological regulatory events that are not revealed by this study.

Figure 1B:
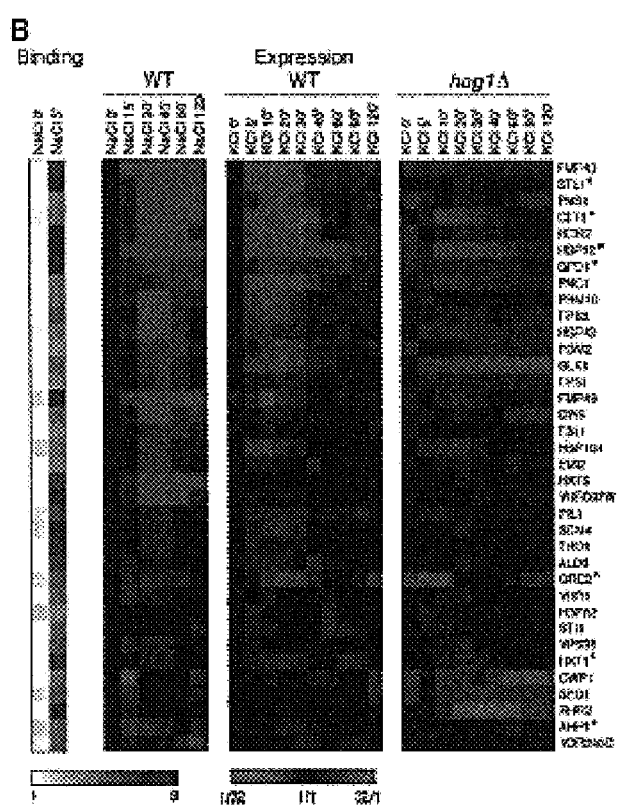

Hog1. We found that 45 genes (P<0.001) were occupied by Hog1p in response to osmotic stress (Table S2). Of the 45 genes, 36 were found to be induced by exposure to NaCl or KCl (FIG. 1B). It is possible that genes that were bound by Hog1p and did not show an increase in transcription are nevertheless genuine target genes of Hog1p since Hog1p activity does not only lead to increased transcription but also to gene repression O'Rourke et al. (O'Rourke, et al., supra). Because the mechanisms of this repression are unknown however, we did not include these genes in FIG. 1.

Fus3, Kss1 and Step5. After exposure of cells to mating pheromone, 29 genes were occupied by Fus3p (Table S3), 9 of which also showed increased transcription. In the case of Kss1p, 14 genes were occupied (Table S4) and 8 of these genes showed increased transcription. Finally, Ste5p occupied 27 genes (Table S5), 12 of which showed increased transcription after pheromone exposure. We could not find evidence that genes that are bound but do not increase in transcription in response to pheromone are true positives. Rather, we found evidence that they represent false positives that were detected due to an inherent bias towards detection of highly expressed genes. When we examined the binding profile of untagged control strains, we found that some highly expressed genes displayed a mild ChIP enrichment over their ORF. When we subtracted the control experiments from the kinase binding experiments done under the same condition, we still found the mating genes bound (those displayed in FIG. 2) but many other previously identified genes were no longer bound. However, this method appeared to increase the overall noise in the data and created additional false positives. Therefore, we did not use data subtraction for our data display.

Tpk1 and Tpk2. We found a good overall correlation between binding and gene expression for Tpk1p. Regions bound by Tpk2 almost exclusively belonged to promoters of ribosomal genes (Table S6). Thus, in both cases, we did not find evidence of false positives.

H. Experiments with Additional Kinases

We also performed ChIP-chip experiments with the MAPK Slt2p of the cell wall integrity pathway under conditions where Slt2p is active (during cell cycle and pheromone exposure) but did not find evidence for gene occupancy. Likewise, we did not find evidence that the PKA subunit Tpk3p is associated with the genome.

I. Patterns of Kinase Occupancy

To gain insights into the mechanisms by which signaling kinases may become associated with the genome, we compared the binding profiles of the kinases across individual genes with profiles of previously studied factors (Pokholok et al., supra). Tpk2p and Hog1p occupancy was greatest at promoters where DNA-binding transcription factors and promoter-associated chromatin regulators bind. In contrast, Fus3p, Kss1p, and Tpk1p showed greatest occupancy over the transcribed regions of genes where transcription elongation factors, gene-associated chromatin regulators, certain histone modifications and nuclear core components are found.

J. Comparison with Genome-Wide ChIP-Chip Data of Transcription Factors

To identify the transcriptional regulators that may recruit Hog1p, Fus3p, Kss1p, and Tpk2p to target genes, we systematically compared the genes occupied by signaling kinases with those occupied by transcriptional regulators (C. T. Harbison et al., Nature 431, 99-104 (Sep. 2, 2004)) (Table S7).

TABLE S1

Interactions between signaling pathways and transcriptional regulators.

| Kinase and condition | Transcriptional regulator and condition | P-value from hypergeometric test | Genes present in both data sets | Number of kinase targets | Number of regulator targets | Over lap |
|---|---|---|---|---|---|---|
| Hog1 salt | SKO1_YPD | 3.27E−08 | 4966 | 44 | 12 | 5 |
| Fus3 alpha | STE12_YPD | 1.93E−12 | 5317 | 29 | 49 | 9 |
| Fus3 alpha | DIG1_YPD | 4.36E−10 | 5249 | 29 | 35 | 7 |
| Fus3 alpha | STE12_Alpha | 1.14E−09 | 5317 | 29 | 97 | 9 |
| Fus3 alpha | STE12_BUT14 | 6.73E−09 | 5308 | 29 | 118 | 9 |
| Fus3 alpha | STE12_BUT90 | 1.12E−08 | 5304 | 29 | 86 | 8 |
| Fus3 alpha | DIG1_BUT90 | 2.77E−08 | 5275 | 29 | 36 | 6 |
| Fus3 alpha | RAP1_YPD | 9.44E−06 | 5162 | 28 | 147 | 7 |
| Kss1 alpha | STE12_YPD | 4.28E−16 | 5317 | 14 | 49 | 9 |
| Kss1 alpha | STE12_Alpha | 2.85E−13 | 5317 | 14 | 97 | 9 |
| Kss1 alpha | STE12_BUT14 | 1.26E−10 | 5308 | 14 | 118 | 8 |
| Kss1 alpha | STE12_BUT90 | 7.21E−10 | 5304 | 14 | 86 | 7 |
| Kss1 alpha | DIG1_Alpha | 2.99E−09 | 5297 | 14 | 56 | 6 |
| Kss1 alpha | DIG1_YPD | 1.88E−08 | 5249 | 14 | 35 | 5 |
| Kss1 alpha | DIG1_BUT90 | 2.13E−08 | 5275 | 14 | 36 | 5 |
| Kss1 alpha | TEC1_Alpha | 1.90E−06 | 5310 | 14 | 37 | 4 |
| Ste5 alpha | STE12_Alpha | 1.77E−16 | 5317 | 27 | 97 | 13 |
| Ste5 alpha | STE12_YPD | 1.25E−14 | 5317 | 27 | 49 | 10 |

TABLE S1-continued

Interactions between signaling pathways and transcriptional regulators.

| Kinase and condition | Transcriptional regulator and condition | P-value from hypergeometric test | Genes present in both data sets | Number of kinase targets | Number of regulator targets | Over lap |
|---|---|---|---|---|---|---|
| Ste5 alpha | STE12_BUT14 | 1.23E−10 | 5308 | 27 | 118 | 10 |
| Ste5 alpha | STE12_BUT90 | 1.87E−10 | 5304 | 27 | 86 | 9 |
| Ste5 alpha | TEC1_Alpha | 3.52E−10 | 5310 | 27 | 37 | 7 |
| Ste5 alpha | DIG1_Alpha | 2.65E−07 | 5297 | 27 | 56 | 6 |
| Ste5 alpha | DIG1_YPD | 7.12E−07 | 5249 | 27 | 35 | 5 |
| Ste5 alpha | MCM1_Alpha | 6.85E−06 | 5318 | 27 | 97 | 6 |
| Tpk2 YPD | FHL1_SM | 8.31E−46 | 5308 | 45 | 186 | 36 |
| Tpk2 YPD | FHL1_YPD | 3.10E−45 | 5224 | 41 | 173 | 34 |
| Tpk2 YPD | FHL1_RAPA | 8.87E−43 | 5312 | 45 | 174 | 34 |
| Tpk2 YPD | RAP1_YPD | 5.38E−21 | 5162 | 41 | 147 | 20 |
| Tpk2 YPD | SFP1_SM | 3.18E−18 | 5240 | 44 | 42 | 13 |

This comparison confirmed that the regulator Sko1p is associated with Hog1p occupancy (M. Proft, K. Struhl, Mol Cell 9, 1307-17 (June, 2002)) and indicates that the transcriptional regulators Ste12p, Dig1p and Tec1p are associated with genes occupied by Fus3p and Kss1p, and that the transcriptional regulators Fhl1p, Rap1p and Sfp1p may be involved in the association of Tpk2p with promoters of ribosomal protein genes.

II. RESULTS

A. Identification of Genes Regulated by the Osmotic Response Signal Transduction Pathway To confirm previous reports that the MAPK Hog1p in yeast occupies genes upon exposure of cells to osmotic stress and to identify the complete set of genes that were so occupied, chromatin immunoprecipitation coupled with microarrays (ChIP-Chip) experiments were performed using a yeast strain S. cerevisiae in which endogenous Hog1p has a tandem affinity purification (TAP) tag (See FIG. 1). The presence of the TAP tag was verified for this and all other yeast strains used in this study (data not shown). In cells exposed to 0.4 M NaCl for 5 min (P. M. Alepuz, A. Jovanovic, V. Reiser, G. Ammerer, Mol. Cell. 7, 767 (2001)), 36 genes were identified that were occupied by Hog1p at high confidence and showed increased transcription after exposure to NaCl or KCl (FIG. 1B), and these genes are listed in Table S2, below.

TABLE S2

Genes occupied by Hog1 under osmotic stress

| ORF | Name | Binding ratio | Probes bound | Peak position |
|---|---|---|---|---|
| YBR126C | TPS1 | 2.0 | 2 | Gene overlap |
| YCL040W | GLK1 | 2.5 | 4 | TSS overlap |
| YCR012W | PGK1 | 2.5 | 2 | Gene overlap |
| YDL022W | GPD1 | 7.4 | 13 | TSS overlap |
| YDR074W | TPS2 | 2.9 | 10 | TSS overlap |
| YDR077W | SED1 | 2.7 | 7 | TSS overlap |
| YDR171W | HSP42 | 2.1 | 2 | Gene overlap |
| YDR516C | EMI2 | 2.0 | 2 | Gene overlap |
| YDR536W | STL1 | 7.2 | 10 | TSS overlap |
| YER062C | HOR2 | 5.2 | 11 | TSS overlap |
| YER063W | THO1 | 5.2 | 11 | TSS overlap |
| YFL014W | HSP12 | 6.0 | 6 | TSS overlap |
| YGL037C | PNC1 | 2.2 | 1 | Gene overlap |
| YGR049W | SCM4 | 8.4 | 15 | TSS overlap |
| YGR052W | FMP48 | 8.4 | 15 | TSS overlap |
| YGR086C | PIL1 | 3.5 | 8 | TSS overlap |

TABLE S2-continued

Genes occupied by Hog1 under osmotic stress

| ORF | Name | Binding ratio | Probes bound | Peak position |
|---|---|---|---|---|
| YGR088W | CTT1 | 2.3 | 6 | TSS overlap |
| YGR243W | FMP43 | 4.1 | 4 | TSS overlap |
| YHR033W | YHR033W | 3.0 | 2 | TSS overlap |
| YHR087W | YHR087W | 6.9 | 8 | TSS overlap |
| YHR094C | HXT1 | 4.2 | 15 | TSS overlap |
| YHR096C | HXT5 | 4.2 | 15 | TSS overlap |
| YIL056W | YIL056W | 2.3 | 1 | proximity: 479 |
| YIL053W | RHR2 | 5.5 | 6 | TSS overlap |
| YJL108C | PRM10 | 2.3 | 4 | TSS overlap |
| YKL096W | CWP1 | 2.3 | 4 | TSS overlap |
| YKL060C | FBA1 | 2.1 | 2 | Gene overlap |
| YLL026W | HSP104 | 2.2 | 7 | Gene overlap |
| YLR109W | AHP1 | 2.5 | 1 | TSS overlap |
| YLR417W | VPS36 | 2.7 | 1 | TSS overlap |
| YML100W | TSL1 | 1.9 | 1 | Gene overlap |
| YMR038C | CCS1 | 2.8 | 1 | Gene overlap |
| YMR105C | PGM2 | 1.8 | 1 | Gene overlap |
| YMR252C | YMR252C | 2.8 | 2 | proximity: 465 |
| YOL151W | GRE2 | 2.7 | 3 | TSS overlap |
| YOL109W | ZEO1 | 2.1 | 1 | Gene overlap |
| YOR027W | STI1 | 2.5 | 8 | Gene overlap |
| YOR028C | CIN5 | 2.5 | 8 | Gene overlap |
| YOR153W | PDR5 | 2.1 | 1 | Gene overlap |
| YOR161C | PNS1 | 2.1 | 1 | Gene overlap |
| YOR246C | YOR246C | 2.8 | 2 | proximity: 39 |
| YOR298W | YOR298W | 2.6 | 2 | Gene overlap |
| YPL240C | HSP82 | 1.8 | 1 | Gene overlap |
| YPL061W | ALD6 | 3.8 | 8 | TSS overlap |
| YPR149W | NCE102 | 3.1 | 4 | TSS overlap |

Figure 1C:
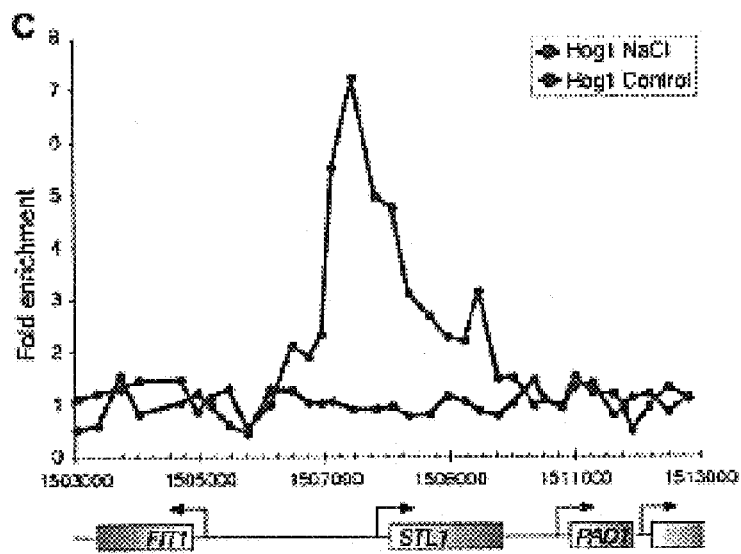

Among these identified genes were all of the seven genes previously found to be occupied by Hog1p (Alepuz et al, supra; M. Proft, K. Struhl, Mol. Cell. 9, 1307 (2002); and L. Tomas-Cobos, L. Casadome, G. Mas, P. Sanz, F. Posas, J. Biol. Chem. 279, 22010 (2004)) (FIG. 1B). Little occupancy of Hog1p was detected at genes before osmotic stress, which finding is consistent with evidence that Hog1p is translocated into the nucleus during osmotic stress (W. K. Huh et al., Nature 425, 686 (2003); P. Ferrigno, F. Posas, D. Koepp, H. Saito, P. A. Silver, EMBO J. 17, 5606 (1998); and S. M. O'Rourke, I. Herskowitz, E. K O'Shea, Trends Genet 18, 405 (2002)). Most genes that were occupied by Hog1p during osmotic stress showed an altered expression pattern in cells lacking Hog1p (FIG. 1B). Hog1p occupancy was highest at the promoters of genes but was also observed throughout the entire transcribed region of these genes (FIG. 1C).

Figure 2A:
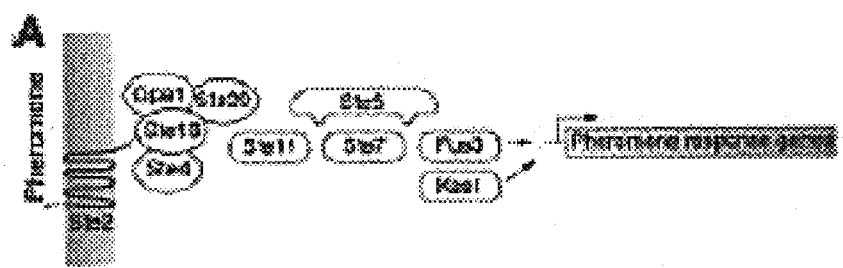
FIGS. 2A to 2G. Recruitment of Fus3p, Kss1p, and Ste5p to genes expressed in response to alpha pheromone treatment.
Figures 2B, 2C, 2D, 2E, 2F, 2G:
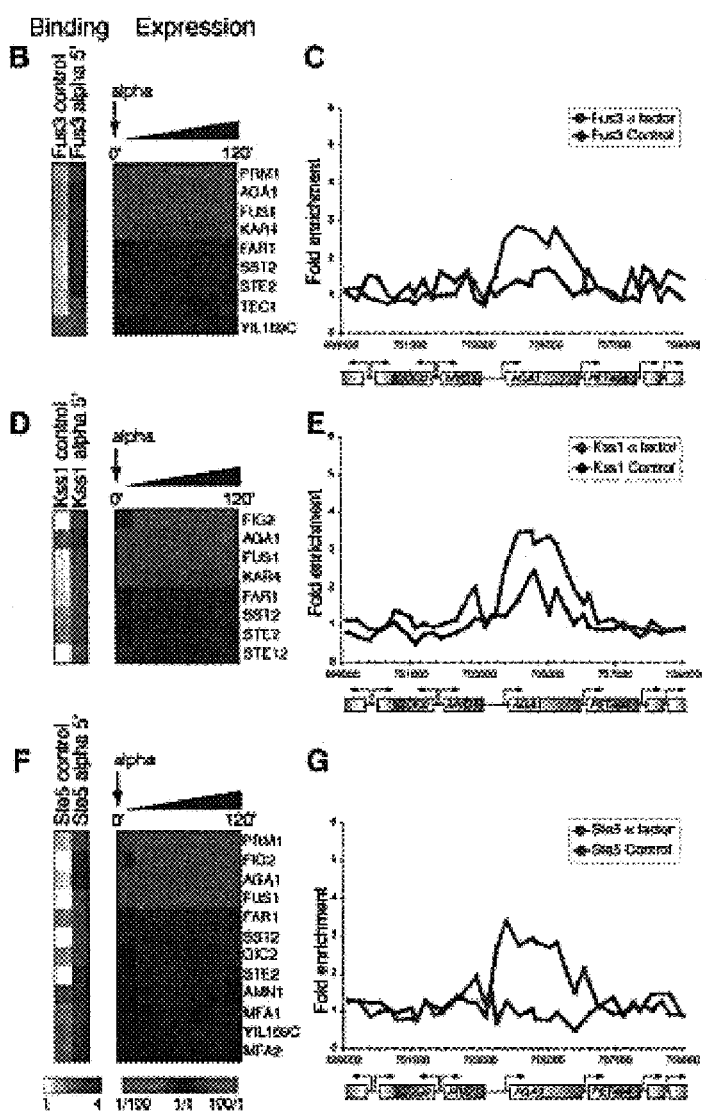

B. Identification of Genes Regulated by the Pheromone Response Signal Transduction Pathway To identify genes regulated by the pheromone response signal transduction pathway in *S. cerevisiae*, applicants determined the chromosomal localization of signal transduction proteins. The MAPKs Fus3p and Kss1p are activated in response to pheromone exposure and induce the expression of mating genes in yeast (M. A. Schwartz, H. D. Madhani, Annu. Rev. Genet. 38, 725 (2004)) (FIG. 2A). A genome-wide ChIP-Chip analysis was used to determine whether Fus3p and Kss1p occupy a specific set of genes upon activation (FIGS. 2A to 2E). Nine genes were found to be occupied by Fus3p and showed increased transcription within 5 min after exposure to mating pheromone (FIG. 2B). Essentially the same set of genes was found to be occupied by Kss1p (FIG. 2D). These genes were previously shown to be dependent on the pheromone MAPK pathway for their expression (C. J. Roberts et al., Science 287, 873 (2000)). Enrichment of both kinases was observed throughout the transcribed regions of these genes (FIGS. 2, C and E).

Ste5p, the central scaffold protein of the pheromone response pathway, interacts with Fus3p and possibly Kss1p at the plasma membrane but can also be found in the nucleus (Kuh et al., supra, Schwartz et al., supra and S. K. Mahanty, Y. Wang, F. W. Farley, E. A. Elion, Cell 98, 501 (1999)). We found that TAP-tagged Ste5p occupied essentially the same mating genes that were bound by Fus3p and Kss1p (FIG. 2F). Ste5p was observed throughout the transcribed regions of these genes (FIG. 2G). These results indicate that Ste5p may function as an adaptor for protein-protein interactions both at the plasma membrane and in the nucleus.

Genes bound by Fus3p, Kss1p and Ste5p are also listed in Tables S3 to S5.

TABLE S3

Genes occupied by Fus3 during response to pheromone

| ORF | Name | Binding ratio | Probes bound | Peak position |
|---|---|---|---|---|
| YBR083W | TEC1 | 2.0 | 1 | Gene overlap |
| YCL055W | KAR4 | 2.8 | 3 | TSS overlap |
| YCL027W | FUS1 | 2.4 | 5 | Gene overlap |
| YCR024C | YCR024C | 2.5 | 2 | proximity: 340 |
| YDR064W | RPS13 | 3.0 | 3 | TSS overlap |
| YER012W | PRE1 | 2.3 | 1 | proximity: 629 |
| YFL026W | STE2 | 3.1 | 3 | TSS overlap |
| YGL103W | RPL28 | 2.4 | 2 | TSS overlap |
| YGL008C | PMA1 | 2.3 | 2 | Gene overlap |
| YIL169C | YIL169C | 1.9 | 1 | Gene overlap |
| YIL123W | SIM1 | 2.6 | 1 | Gene overlap |
| YIL015W | BAR1 | 2.7 | 5 | TSS overlap |
| YJL191W | RPS14B | 2.4 | 1 | Gene overlap |
| YJL157C | FAR1 | 2.7 | 3 | Gene overlap |
| YJL148W | RPA34 | 2.6 | 2 | TSS overlap |
| YJL029C | VPS53 | 2.3 | 1 | proximity: 24 |
| YLR028C | ADE16 | 1.9 | 1 | Gene overlap |
| YLR044C | PDC1 | 2.0 | 1 | Gene overlap |
| YLR452C | SST2 | 2.7 | 3 | Gene overlap |
| YML073C | RPL6A | 2.1 | 1 | Gene overlap |
| YMR271C | URA10 | 2.2 | 2 | proximity: 572 |
| YNL288W | CAF40 | 2.1 | 1 | proximity: 711 |
| YNL286W | CUS2 | 2.2 | 1 | proximity: 908 |
| YNL279W | PRM1 | 2.1 | 2 | TSS overlap |
| YNR044W | AGA1 | 2.8 | 6 | TSS overlap |
| YOL127W | RPL25 | 2.5 | 1 | Gene overlap |
| YOL109W | ZEO1 | 2.8 | 2 | proximity: 434 |
| YOR063W | RPL3 | 2.1 | 3 | Gene overlap |
| YPL061W | ALD6 | 2.2 | 2 | Gene overlap |

TABLE S4

Genes occupied by Kss1 during response to pheromone

| ORF | Name | Binding ratio | Probes bound | Peak position |
|---|---|---|---|---|
| YCL055W | KAR4 | 2.4 | 1 | Gene overlap |
| YCL027W | FUS1 | 2.5 | 6 | TSS overlap |
| YCR089W | FIG2 | 2.8 | 9 | Gene overlap |
| YFL026W | STE2 | 2.7 | 4 | TSS overlap |
| YGL008C | PMA1 | 2.6 | 1 | Gene overlap |
| YHL034C | SBP1 | 2.4 | 1 | proximity: 648 |
| YHR084W | STE12 | 2.3 | 2 | Gene overlap |
| YIL015W | BAR1 | 2.7 | 7 | TSS overlap |
| YJL157C | FAR1 | 2.3 | 2 | Gene overlap |
| YLR452C | SST2 | 2.4 | 2 | Gene overlap |
| YMR013C | SEC59 | 1.9 | 2 | proximity: 734 |
| YNL278W | CAF120 | 2.0 | 2 | TSS overlap |
| YNR044W | AGA1 | 3.4 | 6 | TSS overlap |
| YOL109W | ZEO1 | 2.5 | 2 | Gene overlap |

TABLE S5

Genes occupied by Ste5 during response to pheromone

| ORF | Name | Binding ratio | Probes bound | Peak position |
|---|---|---|---|---|
| YBR158W | AMN1 | 2.5 | 3 | TSS overlap |
| YCL027W | FUS1 | 2.0 | 4 | Gene overlap |
| YCR089W | FIG2 | 3.2 | 10 | TSS overlap |
| YDR064W | RPS13 | 2.3 | 2 | Gene overlap |
| YDR086C | SSS1 | 2.1 | 2 | Gene overlap |
| YDR309C | GIC2 | 2.0 | 1 | Gene overlap |
| YDR461W | MFA1 | 2.4 | 3 | TSS overlap |
| YFL026W | STE2 | 2.7 | 5 | TSS overlap |
| YGL030W | RPL30 | 2.2 | 1 | Gene overlap |
| YGL008C | PMA1 | 2.8 | 2 | TSS overlap |
| YGR038W | ORM1 | 2.2 | 1 | proximity: 783 |
| YGR106C | YGR106C | 1.9 | 1 | proximity: 816 |
| YIL169C | YIL169C | 2.6 | 1 | Gene overlap |
| YIL015W | BAR1 | 2.5 | 4 | Gene overlap |
| YJL157C | FAR1 | 2.0 | 1 | Gene overlap |
| YJL148W | RPA34 | 2.5 | 2 | proximity: 294 |
| YJR123W | RPS5 | 2.3 | 1 | Gene overlap |
| YKR042W | UTH1 | 2.7 | 1 | Gene overlap |
| YLR355C | ILV5 | 2.8 | 3 | Gene overlap |
| YLR452C | SST2 | 2.0 | 1 | Gene overlap |
| YMR271C | URA10 | 2.1 | 1 | proximity: 572 |
| YNL279W | PRM1 | 2.1 | 2 | Gene overlap |
| YNL145W | MFA2 | 3.1 | 2 | TSS overlap |
| YNL067W | RPL9B | 1.8 | 1 | proximity: 619 |
| YNR044W | AGA1 | 3.4 | 7 | TSS overlap |
| YOL155C | YOL155C | 2.3 | 4 | proximity: 374 |
| YOL109W | ZEO1 | 2.8 | 2 | Gene overlap |

C. Identification of Genes Regulated by the cAMP-Dependent Pathway

To identify genes regulated by the glucose-sensing cAMP-dependent pathway of in *S. cerevisiae*, applicants determined the chromosomal localization of several signal transduction proteins.

Figure 3A:
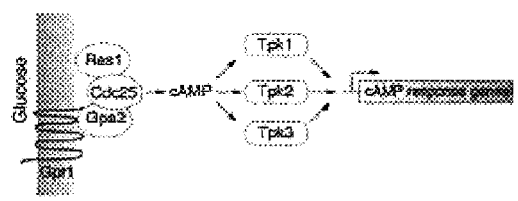
FIGS. 3A to 3G. Occupancy of transcribed regions of active genes by Tpk1p and of promoters of ribosomal protein genes by Tpk2p.
Figure 3B:
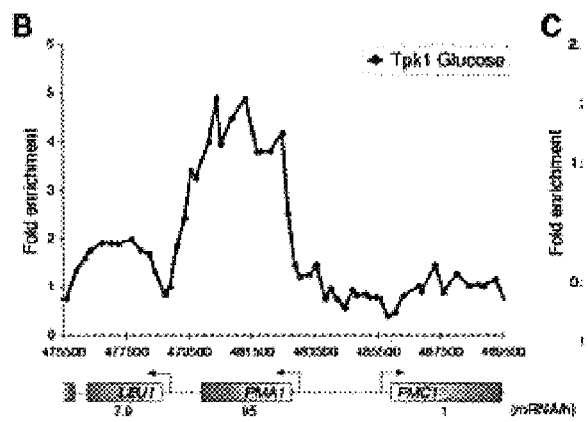
Figure 3C:
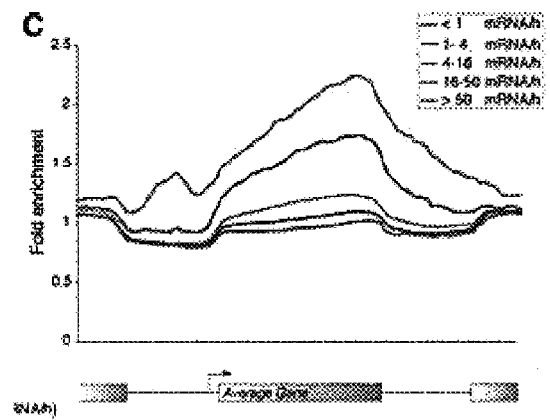
Figure 3D:
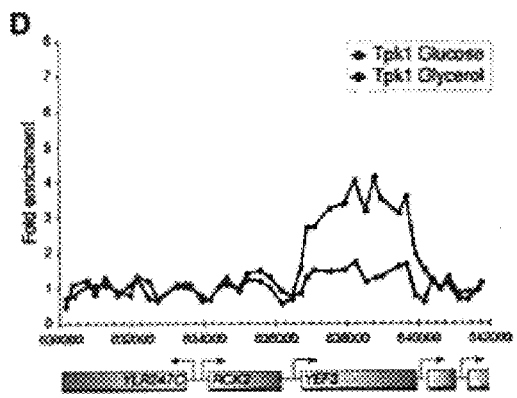
Figure 3E:
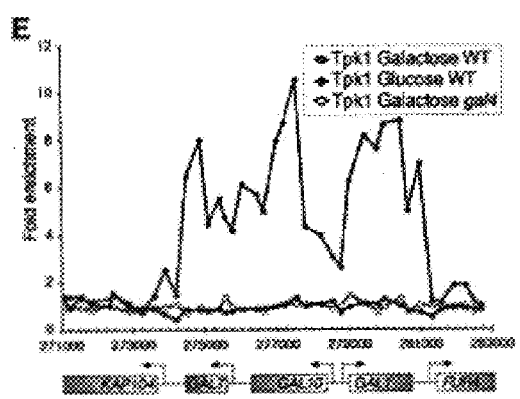

The cyclic adenosine monophosphate (cAMP)-activated protein kinase A (PKA) is stimulated by an increased concentration of intracellular cAMP when yeast are exposed to fermentable carbon sources such as glucose (FIG. 3A)(L. Schneper, K. Duvel, J. R. Broach, Curr. Opin. Microbiol. 7, 624 (2004)). There are three PKA catalytic subunits in yeast: Tpk1p, Tpk2p, and Tpk3p. Genome-wide ChIP-Chip analyses suggested that Tpk1p occupies the entire transcribed region of most actively transcribed genes in cells grown in glucose media (FIGS. 3B and 3C). To further test this possibility, we determined whether Tpk1p occupancy would change at genes that were dynamically repressed or activated as yeast cells were subjected to different environmental conditions. Indeed, Tpk1p occupancy was reduced at genes whose expression was reduced when cells were transferred to a nonfermentable carbon source (glycerol) (FIG. 3D). In contrast, Tpk1p became associated with genes that were activated when cells were exposed to galactose (FIG. 3E). Occupancy at these galactose-inducible genes was dependent on gene activation because it was not detected in strains lacking the transcriptional activator Gal4p (FIG. 3E). Additional genes to which Tpk1p becomes associated are shown in FIG. 3G. These results confirm that Tpk1p generally becomes physically associated with actively transcribed genes and that occupancy occurs throughout the transcribed portions of these genes.

We then investigated whether Tpk2p occupies specific portions of the genome. Tpk2p was found almost exclusively associated with the promoters of ribosomal protein genes (See FIG. 3F, and table S6).

TABLE S6

Genes occupied by Tpk2

| ORF | Name | Ratio H2O2 | Ratio Glucose |
|---|---|---|---|
| YAL038W | CDC19 | 1.90 | |
| YBL093C | RPL32 | 4.25 | |
| YBL087C | RPL23A | 2.68 | |
| YBL027W | RPL19B | 12.43 | 5.18 |
| YBR048W | RPS11B | 12.51 | 8.82 |
| YBR084C | RPL19A | 9.19 | 5.22 |
| YBR118W | TEF2 | 4.82 | 3.35 |
| YBR181C | RPS6B | 5.80 | |
| YBR189W | RPS9B | 10.28 | 5.80 |
| YBR191W | RPL21A | 7.16 | |
| YCR031C | RPS14A | 3.40 | |
| YDL191W | RPL35A | 8.86 | 3.97 |
| YDL184C | RPL41A | 5.07 | 4.08 |
| YDL136W | RPL35B | 4.63 | 3.46 |
| YDL130W | RPP1B | 7.98 | 3.37 |
| YDL082W | RPL13A | 5.49 | 2.56 |
| YDL075W | RPL31A | 3.68 | |
| YDL060W | TSR1 | 10.94 | 9.48 |
| YDR500C | RPL37B | 3.42 | 2.32 |
| YER056C | RPL34A | 2.49 | |
| YER074W | RPS24A | 8.95 | 5.27 |
| YER101C | AST2 | 2.90 | |
| YER117W | RPL23B | 10.29 | |
| YER131W | RPS26B | 6.19 | 3.42 |
| YFL034C | RPL22B | 4.13 | 4.40 |
| YFR032C | RPL29 | 5.38 | |
| YFR033C | QCR6 | 4.81 | |
| YGL189C | RPS26A | 3.51 | 2.57 |
| YGL136C | MRM2 | 10.70 | |
| YGL123W | RPS2 | 2.64 | |
| YGL076C | RPL7A | 4.53 | |
| YGL030W | RPL30 | 3.69 | |
| YGR027C | RPS25A | 6.15 | 3.68 |
| YGR118W | RPS23A | 4.66 | 2.58 |
| YGR148C | RPL24B | 4.57 | |
| YGR214W | RPS0A | 6.63 | |
| YGR254W | ENO1 | 2.17 | |
| YHL015W | RPS20 | 9.52 | 4.81 |
| YHL001W | RPL14B | 4.62 | 2.25 |
| YHR010W | RPL27A | 3.74 | |
| YHR055C | CUP1-2 | 2.67 | |
| YHR141C | RPL42B | 3.69 | |
| YHR174W | ENO2 | 2.39 | |
| YHR203C | RPS4B | 4.51 | |
| YIL148W | RPL40A | 2.62 | |
| YIL133C | RPL16A | 4.79 | |
| YIL069C | RPS24B | 9.79 | |
| YJL052C | RPL34B | 3.94 | 2.56 |
| YJL177W | RPL17B | 3.13 | |

TABLE S6-continued

Genes occupied by Tpk2

| ORF | Name | Ratio H2O2 | Ratio Glucose |
|---|---|---|---|
| YJL136C | RPS21B | 8.49 | 3.59 |
| YJL052W | TDH1 | 2.14 | |
| YJR017C | ESS1 | 2.15 | |
| YJR123W | RPS5 | 3.30 | |
| YJR145C | RPS4A | 3.70 | |
| YKL180W | RPL17A | 6.07 | |
| YKL152C | GPM1 | 2.14 | |
| YKL060C | FBA1 | 2.52 | |
| YKR094C | RPL40B | 2.89 | |
| YLL045C | RPL8B | 5.71 | |
| YLL026W | HSP104 | 2.36 | |
| YLR075W | RPL10 | 3.49 | 2.51 |
| YLR185W | RPL37A | 4.57 | |
| YLR287C-A | RPS30A | 5.13 | 4.23 |
| YLR325C | RPL38 | 12.79 | 6.38 |
| YLR344W | RPL26A | 5.13 | 2.70 |
| YLR388W | RPS29A | 1.95 | |
| YLR406C | RPL31B | 3.18 | |
| YLR441C | RPS1A | 1.67 | |
| YML028W | TSA1 | 2.10 | |
| YMR142C | RPL13B | 9.29 | 5.64 |
| YMR143W | RPS16A | 9.29 | |
| YMR242C | RPL20A | 6.01 | |
| YNL302C | RPS19B | 10.96 | |
| YNL178W | RPS3 | 2.56 | |
| YNL162W | RPL42A | 2.48 | |
| YNL096C | RPS7B | 5.67 | 3.18 |
| YNL069C | RPL16B | 6.25 | 3.56 |
| YNL067W | RPL9B | 2.17 | |
| YOL127W | RPL25 | 10.26 | |
| YOL121C | RPS19A | 7.31 | |
| YOL109W | ZEO1 | 2.46 | |
| YOL040C | RPS15 | 6.82 | |
| YOL039W | RPP2A | 6.82 | |
| YOR096W | RPS7A | 2.73 | |
| YOR182C | RPS30B | 18.77 | 11.36 |
| YOR234C | RPL33B | 2.82 | |
| YOR312C | RPL20B | 9.65 | 3.60 |
| YOR369C | RPS12 | 2.96 | |
| YPL249C-A | RPL36B | 2.55 | |
| YPL090C | RPS6A | 4.20 | |
| YPL079W | RPL21B | 5.25 | |
| YPR043W | RPL43A | 5.10 | 2.49 |
| YPR103W | PRE2 | 3.61 | |
| YPR132W | RPS23B | 4.75 | |
| YGL103W | RPL28 | | 3.69 |
| YIL069C | RPS24B | | 2.83 |
| YJL148W | RPA34 | | 1.46 |
| YLR167W | RPS31 | | 2.28 |
| YNL301C | RPL18B | | 4.65 |
| YOL127W | RPL25 | | 5.67 |
| YOL120C | RPL18A | | 4.55 |
| YPL081W | RPS9A | | 4.43 |

Figure 3F:
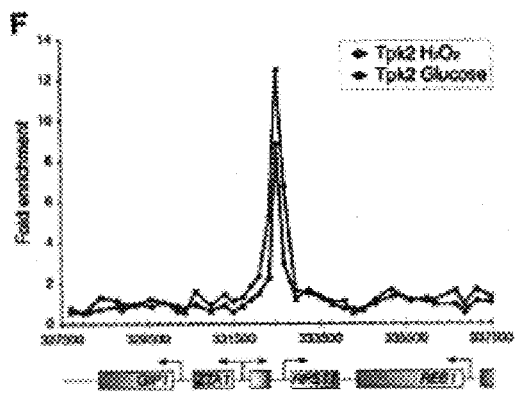
Figure 3G:
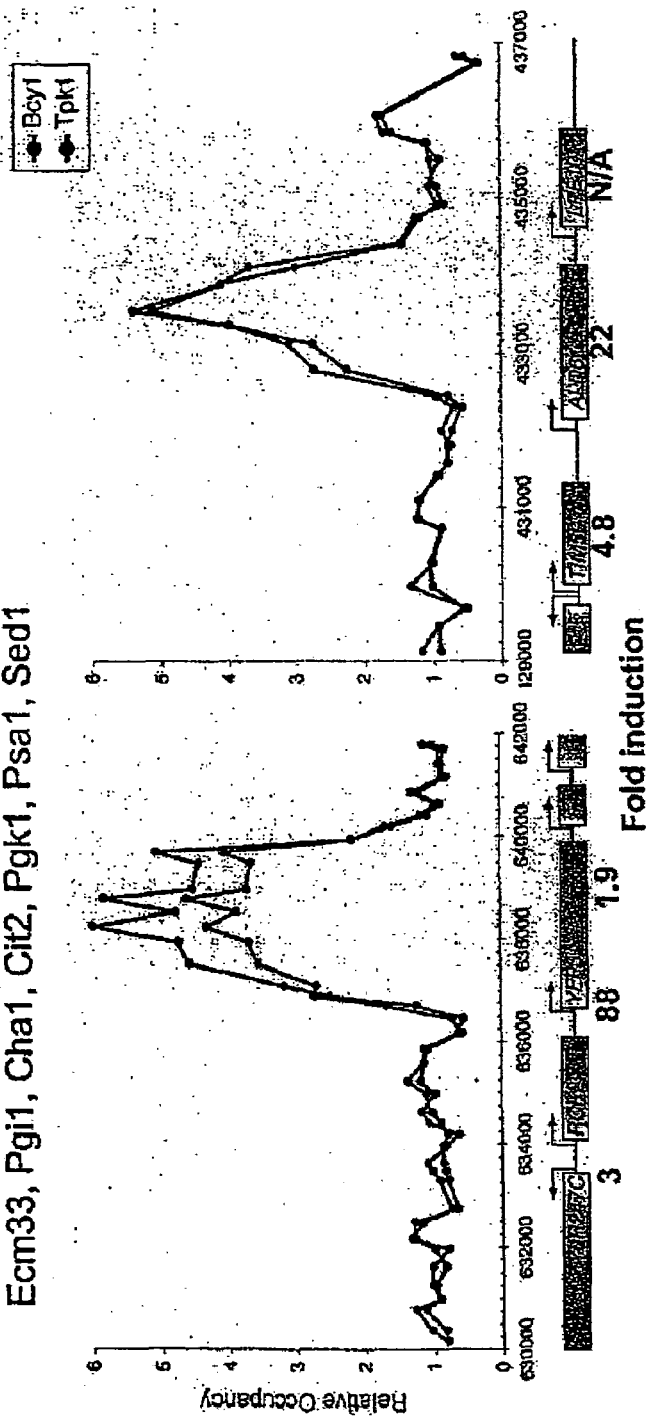
Figure 4:
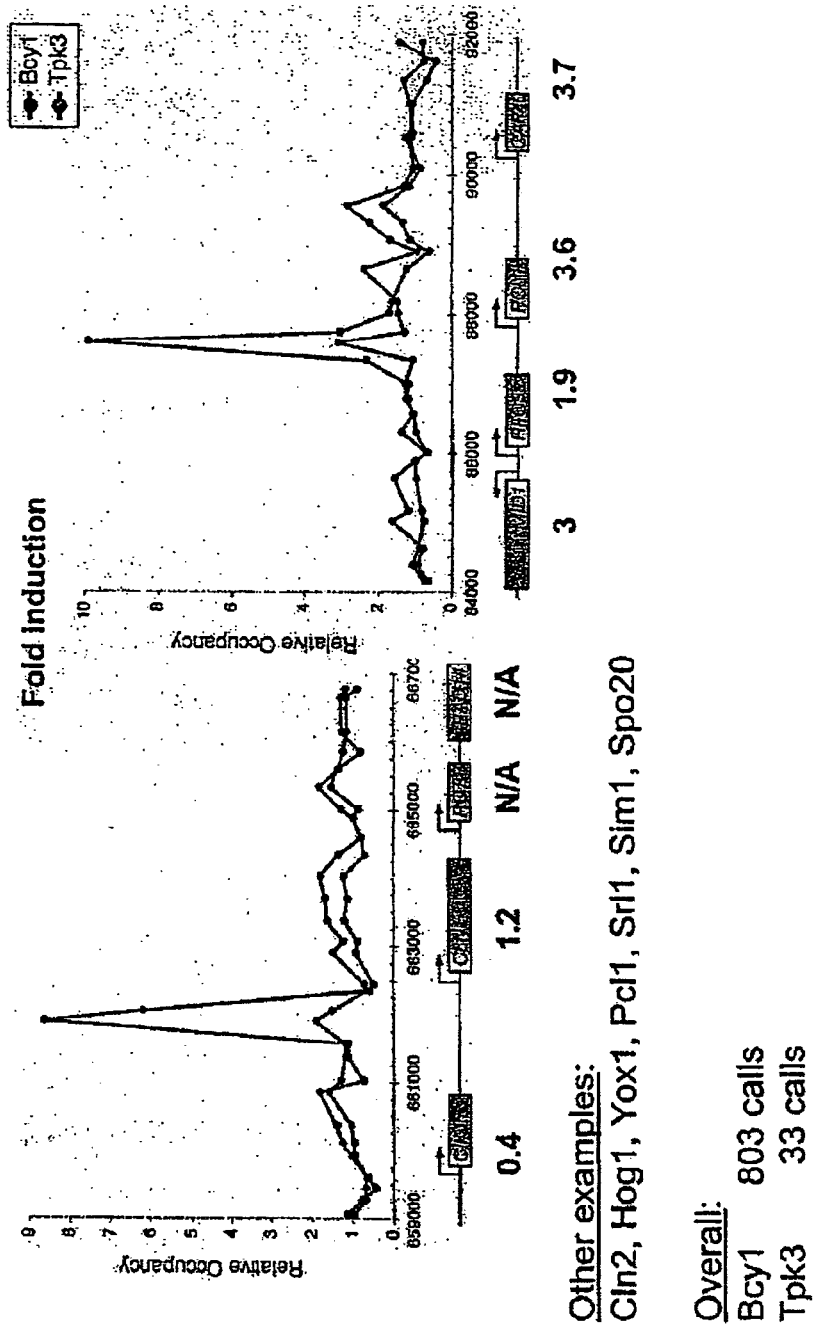
FIG. 4 shows that the catalytic Tpk3 subunit of PKA occupies promoters of cell cycle genes.

Gene occupancy by Tpk2p did not correlate with transcription rates throughout the genome, and Tpk2p remained associated with its target genes when cells were exposed to oxidative stress, which leads to reduced transcription of ribosomal protein genes (FIG. 3F). We did not detect Tpk3p occupancy on chromatin under the conditions used here (rich media, oxidative stress, and pheromone exposure). However, a previous study had shown the catalytic Tpk3 subunit and the Regulatory Bcyl subunit of PKA bound extensively to the promoter regions of cell-cycle genes CLN1 and PCL1, as well as other genes as shown in FIG. 4. See priority application.

Although we have not shown that occupancy of genes by Tpk1p and Tpk2p regulates gene expression, previous studies have shown that PKA phosphorylates the Srb9 subunit of the Mediator complex (Chang, S. C. Howard, P. K. Herman, Mol.

Cell. 15, 107 (2004)) and that PKA activity regulates ribosomal gene expression (C. Klein, K. Struhl, Mol. Cell. Biol. 14, 1920 (1994); D. E. Martin, A. Soulard, M. N. Hall, Cell 119, 969 (2004); and P. Jorgensen et al., Genes Dev. 18, 2491 (2004)). The idea that some PKA family members might operate, at least in part, through occupancy of actively transcribed genes is attractive because it might provide an efficient means for cells to respond to the nutrient environment at the level of gene expression.

III. CONCLUSION

Our finding that most activated MAPKs and PKAs in yeast become associated with distinct target genes changes our perception of the sites at which signaling pathways act to regulate gene expression. With the exception of Hog1p and p38, studies of the effect of signal transduction pathways on gene expression have not implied that the activities of MAPKs or PKAs involve genome occupancy. Although it is still possible that the phosphorylation of transcriptional regulators also occurs elsewhere in the cell, the detection of kinases by ChIP-Chip analyses at target genes demonstrates a model in which regulation by signal transduction kinases often occurs at the genes themselves. In this model, kinases become physically localized at specific sites in the genome by association with transcription factors, chromatin regulators, the transcription apparatus, nucleosomes, or nuclear pore proteins that are associated with subsets of actively transcribed genes.

The kinases studied here associate with target genes in at least three different patterns, suggesting that there are different mechanisms involved in their association with genes. Tpk2p was found only at the promoter regions of its target genes. Hog1p occupancy was greatest at the promoters but also occurred to a limited extent within the transcribed regions of genes. Fus3p, Kss1p, and Tpk1p showed the greatest occupancy over the transcribed regions of genes. ChIP-Chip experiments show that DNA binding transcription factors and promoter-associated chromatin regulators generally occupy the promoters of genes, whereas transcription elongation factors, gene-associated chromatin regulators, certain histone modifications, and nuclear pore proteins are found enriched along the transcribed regions of genes. Preferential binding to these factors could explain the localization of the kinases.

Many features of signal transduction pathways are highly conserved in eukaryotes, so it is reasonable to expect that MAPKs and PKAs of higher eukaryotes may also be found to occupy genes that they regulate. Indeed, a human homolog of Hog1p, p38, occupies and activates the myogenin (MYOG) and muscle-creatine kinase (CKM) promoters during human myogenesis. The observation that components of many signal transduction pathways physically occupy their target genes upon activation should facilitate the mapping of the regulatory circuitry that eukaryotic cells use to modify gene expression in response to a broad range of environmental cues.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of identifying at least one gene that is regulated by a signaling pathway that comprises at least one polypeptide, wherein said polypeptide is not a known DNA binding polypeptide and is not predicted to bind DNA because it lacks a known DNA binding domain, said method comprising:
   (a) producing a mixture comprising DNA fragments to which said polypeptide is bound in a cell;
   (b) isolating one or more DNA fragments to which said polypeptide is bound from the mixture produced in step (a), wherein said isolating is carried out by using an agent that specifically binds to said polypeptide;
   (c) identifying regions of the genome which are complementary to the DNA fragments isolated in step (b); and
   (d) identifying at least one gene operably-linked to a region of the genome identified in step (c) to identify at least one gene that is regulated by said signaling pathway.

2. The method according to claim 1, wherein the signaling pathway is a pathway which is activated by the binding of a ligand to a transmembrane receptor.

3. The method according to claim 2, wherein said polypeptide is an enzyme.

4. The method according to claim 3, wherein said polypeptide is a kinase.

5. The method according to claim 4, wherein said kinase is a MAPK.

6. The method according to claim 1, wherein said method further comprises, between steps (b) and (c), generating a probe from the one or more of the isolated DNA fragments.

7. The method according to claim 6, wherein said probe is labeled with a fluorescent label.

8. The method according to claim 6, wherein said identifying step (c) comprises combining said probe with one or more sets of distinct nucleic acid features bound to a surface of a solid support.

9. The method according to claim 8, wherein said distinct nucleic acid features are each complementary to a region of the genome.

10. The method according to claim 8, wherein said distinct nucleic acid features are complementary to locations in the genome that are substantially evenly spaced.

11. The method according to claim 8, wherein said nucleic acid features bound to a surface of a solid support include sequences representative of locations distributed across at least a portion of a genome.

12. The method according to claim 11, wherein said portion of the genome comprises at least 20% of the genome.

13. The method according to claim 8, wherein said sets of distinct nucleic acid features comprise an addressable array.

14. The method according to claim 1, wherein steps (a) and (b) are performed in a first location, and steps (c) and/or (d) is performed in a second location.

15. The method according to claim 14, wherein said first location is remote to said second location.

16. The method according to claim 1, further comprising transmitting a result from identifying regions of a genome from a first location to a second location or vice versa.

17. The method according to claim 1, wherein said genome is from a eukaryotic cell.

18. The method according to claim 17, wherein said cell is derived from a tissue biopsy.

19. The method according to claim 18, wherein said tissue biopsy is from a subject afflicted with, or suspected of being afflicted with, a disorder.

20. The method according to claim 17, wherein said cell has been treated with an agent.

21. The method according to claim 1, wherein said genome is from a first cell and said polypeptide is from a second cell.

22. The method of claim 1, wherein said agent is an antibody.

* * * * *